United States Patent
Portal et al.

(10) Patent No.: US 8,044,082 B2
(45) Date of Patent: Oct. 25, 2011

(54) N-PHENYLACETAMIDE INHIBITORS OF THE ENZYME SOAT-1 AND PHARMACEUTICAL/COSMETIC COMPOSITIONS COMPRISED THEREOF

(75) Inventors: Thibaud Portal, Opio (FR); Laurence Dumais, Le Rouret (FR); Jérôme Aubert, Grasse (FR); Laurent Lamy, Nice (FR)

(73) Assignee: Galderma Research & Development, Biot (FR)

( * ) Notice: Subject to any disclaimer, the term of this patent is extended or adjusted under 35 U.S.C. 154(b) by 0 days.

(21) Appl. No.: 12/718,239

(22) Filed: Mar. 5, 2010

(65) Prior Publication Data

US 2010/0247583 A1 Sep. 30, 2010

Related U.S. Application Data

(63) Continuation of application No. PCT/EP2008/061773, filed on Sep. 5, 2008.

(60) Provisional application No. 60/960,097, filed on Sep. 14, 2007.

(30) Foreign Application Priority Data

Sep. 6, 2007 (FR) ...................................... 07 57394

(51) Int. Cl.
*A61K 31/4166* (2006.01)
*C07D 235/02* (2006.01)
*C07D 233/72* (2006.01)

(52) U.S. Cl. ..................... 514/389; 514/391; 548/301.4; 548/319.5

(58) Field of Classification Search ............... 548/319.5, 548/324.1, 300.7, 301.4; 514/386, 389, 391, 514/392, 387
See application file for complete search history.

(56) References Cited

U.S. PATENT DOCUMENTS

2007/0197617 A1 8/2007 Chen et al.

FOREIGN PATENT DOCUMENTS

| EP | 0 987 254 A1 | 3/2000 |
| EP | 1 421 294 A1 | 6/2004 |
| JP | 2007-176809 | 7/2007 |
| WO | WO 2005/082879 | 9/2005 |
| WO | WO 2007/061880 A1 | 5/2007 |

OTHER PUBLICATIONS

Vippagunta et al., Crystalline solids, 2001, Advanced Drug Delivery Reviews, 48, pp. 3 and 18.*
Peterson et al., Expanding the scope of Crystal form evaluation in Pharmaceutical Science, 2006, J Pharm Pharmaceut Sci, 9(3), pp. 317-326.*
Patrick M. O'Brien et al., "Inhibitors of Acyl-CoA:Cholesterol O-Acyltransferase. Synthesis and Pharmacological Activity of (±)-2-Dodecyl-α-phenyl-N-(2,4,6-trimethoxyphenyl)-2H-tetrazole-5-actamide and Structurally Related Tetrazole Amide Derivatives," *Journal of Medicinal Chemistry*, Mar. 4, 1996, pp. 2354-2366, vol. 39, No. 12, American Chemical Society.
Andrew D. White et al., "Heterocyclic Amides: Inhibitors of Acyl-CoA:Cholesterol O-Acyl Transferase with Hypocholesterolemic Activity in Several Species and Antiatherosclerotic Activity in the Rabbit," *Journal of Medicinal Chemistry*, Jun. 6, 1996, pp. 3908-3919, vol. 39, No. 20, American Chemical Society.
Patrick M. O'Brien et al., "Inhibitors of Acyl-CoA:Cholesterol O-Acyl Transferase (ACAT) as Hypocholesterolemic Agents. 8.[1] Incorporation of Amide of Amine Functionalities into a Series of Disubstituted Ureas and Carbamates. Effect on ACAT Inhibition in Vitro and Efficacy in Vivo," *Journal of Medicinal Chemistry*, Dec. 20, 1993, pp. 1810-1822, vol. 37, No. 12, American Chemical Society.
Bharat Trivedi et al., Inhibitors of Acyl-CoA:Cholesterol Acyltransferase. 4. A Novel Series of Urea ACAT Inhibitors as Potential Hypocholesterolemic Agents,: *Journal of Medicinal Chemistry*, May 20, 1993, pp. 3300-3307, vol. 36, No. 22, American Chemical Society.
Corinne Augelli-Szafran et al., "Imidazolidinones and Pyrazolones As Novel ACAT Inhinitors: Chemistry and Biological Activity," *Bioorganic & Medicinal Chemistry Letters*, 1994, pp. 1095-1100, vol. 4, No. 9, Elsevier, Great Britain.
R. Bellemin et al., "New Indole Derivatives as ACAT Inhibitors: Synthesis and Structure-Activity Relationships," *European Journal of Medicinal Chemistry*, Jan. 1, 1996, pp. 123-132, vol. 31, No. 2, Editions Scientifique Elsevier, Paris, France.

\* cited by examiner

*Primary Examiner* — Kamal Saeed
*Assistant Examiner* — Kristin Bianchi
(74) *Attorney, Agent, or Firm* — Buchanan Ingersoll & Rooney, P.C.

(57) ABSTRACT

Novel N-phenylacetamide compounds of formula (I):

(I)

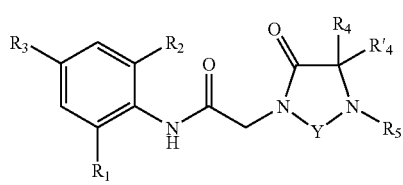

and cosmetic and pharmaceutical compositions containing same are useful for treating disorders of the sebaceous gland, e.g., acne, or have cosmetic applications.

24 Claims, No Drawings

N-PHENYLACETAMIDE INHIBITORS OF THE ENZYME SOAT-1 AND PHARMACEUTICAL/COSMETIC COMPOSITIONS COMPRISED THEREOF

CROSS-REFERENCE TO ALL PRIOR APPLICATIONS

This application claims priority under 35 U.S.C. §119 of FR 0757394, filed Sep. 6, 2007 and under 35 U.S.C. §120 of U.S. Provisional Application No. 60/960,097, filed Sep. 14, 2007, and is a continuation/national phase of PCT/EP 2008/061773, filed Sep. 5, 2008 and designating the United States (published in the English language on Mar. 12, 2009 as WO 2009/030747 A1), each hereby expressly incorporated by reference in its entirety and each assigned to the assignee hereof.

BACKGROUND OF THE INVENTION

1. Technical Field of the Invention

The present invention relates to novel N-phenylacetamide compound inhibitors of the enzyme SOAT-1 (Sterol-O-Acyl Transferase-1), likewise named ACAT-1 (Acylcoenzyme A Cholesterol Acyl Transferase). It also relates to their formulation into pharmaceutical compositions useful in human or veterinary medicine, or else into cosmetic compositions and, likewise, their non-therapeutic applications.

2. Description of Background and/or Related and/or Prior Art

The compounds having an activity of the type inhibiting SOAT-1 are widely described in the literature as having activities in the regulation of biological processes involving cholesterol and its derivatives. These properties confer to this class of compounds a great potential in the treatment or the prevention of numerous pathologies, and more particularly in dermatology and in cardiovascular diseases or complaints of the central nervous system. The majority of the biological effects of the inhibitors of SOAT-1 are mediated by the prevention of the synthesis of esters of cholesterol by the enzyme SOAT-1. Among the documents of the prior art describing molecules inhibiting SOAT-1, exemplary are WO 96/10559, EP-0370740, EP-0424194, U.S. Pat. No. 4,623,663, EP-0557171, U.S. Pat. No. 5,003,106, EP-0293880, EP-0433662 and U.S. Pat. No. 5,106,873, which describe compounds for treating arteriosclerosis or hypercholesterolaemia to be treated. The therapeutic potential of inhibitors of SOAT-1 in the treatment of cardiovascular diseases and, in particular, of hypercholesterolaemia and of arteriosclerosis is likewise described by Kharbanda R. K. et al., in *Circulation*, 2005, 11, 804. The potential of inhibitors of SOAT-1 for the treatment of Alzheimer's disease has likewise been reported in the literature, for example, by Puglielli, L. et al., in *Nature Neurosciences* 2003, 6 (4), 345.

U.S. Pat. Nos. 6,133,326, 6,271,268 and WO 2005/034931 describe compounds which are inhibitors of SOAT-1 for inhibiting the production of sebum. In the field of dermatology in particular, it is particularly advantageous to prevent the excessive production of sebum and all the associated conditions. Sebum is produced by the sebaceous gland. The greater concentration of sebaceous glands is situated on the face, the shoulders, the back and the scalp. The sebum is secreted on the surface of the skin, where it plays a major physiological role, associated with the maintenance of the cutaneous barrier and of a microenvironment allowing the regulation of the bacterial flora and cutaneous fungus.

The hyperproduction of sebum is, most often, associated with a skin or a scalp of greasy appearance, a cause of discomfort and a degraded appearance. In addition, the hyperproduction of sebum can breed seborrhoeic dermatitis and is associated with an increased incidence or severity of acne. The esters of cholesterol produced in the sebaceous gland by SOAT-1 are one of the components of sebum, among several classes of lipids including the triglycerides, the esters of waxes and the squalenes, as described by Nikkari, T., in *J Invest Derm* 1974, 62, 257. The inhibition of this enzyme or other acyltransferases can thus allow the production of sebum to be inhibited. U.S. Pat. No. 6,133,326 describes, in particular, the inhibition of the sebum by inhibitors of ACAT-1 (likewise named SOAT-1). Nevertheless, to date, no treatment utilizing such inhibitors is available commercially. The only treatments for the disorders linked to hyperseborrhoea to be remedied or relieved are systemic hormonal treatments or systemic treatment with 13-cis-retinoic acid, treatments whose secondary effects considerably limit their field of application. There thus exists a clear cosmetic and medical need for the treatment of disorders and pathologies linked to the hyperproduction of sebum.

SUMMARY OF THE INVENTION

The present invention features novel N-phenylacetamide compounds which are potent inhibitors of the enzyme SOAT-1.

Thus, this invention features novel N-phenylacetamide compound inhibitors of the enzyme SOAT-1, having the following general formula (I):

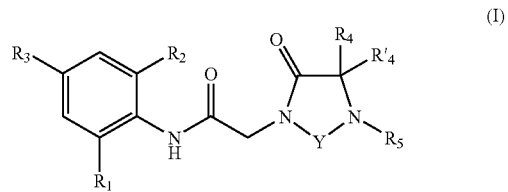

in which:
Y is C(O) or $CH_2$,
$R_1$ is a ($C_1$-$C_6$)alkyl radical,
$R_2$ is a hydrogen, chlorine, fluorine or bromine atom, or a ($C_1$-$C_6$)alkyl radical,
$R_3$ is a hydrogen atom, a ($C_1$-$C_6$)alkyl radical, or a —$WNR_6R_7$ radical wherein W is C(O), C(S) or $CH_2$, $R_6$ is a hydrogen atom or a ($C_1$-$C_6$)alkyl radical and $R_7$ is a hydrogen atom, a cycloalkyl radical or a phenyl radical,
$R_4$ and $R'_4$ are identical and are each a ($C_1$-$C_6$)alkyl radical or else $R_4$ and $R'_4$ are bonded to one another and together form, with the carbon atom from which they depend, a cycloalkyl group,
$R_5$ is a group selected from among:
  (i) an unsubstituted phenyl radical or a phenyl radical substituted by one to three identical or different substituents selected from among the atoms fluorine, chlorine, iodine or bromine, and the radicals ($C_1$-$C_6$)alkyl, hydroxymethyl, mono-, di- or trifluoromethyl, hydroxyl, phenyl, 2-pyridyl, 3-pyridyl or 4-pyridyl, ($C_1$-$C_6$)alkoxy, phenoxy, benzyloxy, mono-, di- or trifluoromethoxy,
  (ii) a ($C_1$-$C_{12}$)alkyl radical, optionally substituted by one or more hydroxyl groups, or fluorine, chlorine, iodine or bromine atoms,
  (iii) a cycloalkyl radical or a —$(CH_2)_m$-cycloalkyl radical in which m is equal to 1, 2 or 3,
  (iv) an aralkyl radical —$(CH_2)_n$—Ar with n equal to 1, 2 or 3 and Ar is an unsubstituted phenyl radical, unsubstituted naphthyl, or a phenyl radical substituted by one to three identical or different substituents selected from among the atoms fluorine, chlorine, iodine or bromine, and the radicals ($C_1$-$C_6$)alkyl, hydroxymethyl, mono-, di- or trifluoromethyl, hydroxyl, phenyl, 2-pyridyl, 3-pyridyl or 4-pyridyl, ($C_1$-$C_6$) alkoxy, phenoxy, benzyloxy, mono-, di- or trifluoromethoxy, as well as their pharmaceutically acceptable salts, solvates or hydrates and their conformers or rotamers.

"Alkyl radical" means a saturated, linear or branched hydrocarbon chain. "$(C_1-C_{12})$alkyl" means an alkyl chain comprising from 1 to 12 carbon atoms.

"$(C_1-C_6)$alkyl" means an alkyl chain comprising from 1 to 6 carbon atoms. Exemplary of $(C_1-C_6)$alkyl are methyl, ethyl, n-propyl, isopropyl, n-butyl, tert-butyl, sec-butyl, pentyl, and hexyl radicals.

"$(C_1-C_4)$alkyl" means an alkyl chain having from 1 to 4 carbon atoms. Exemplary of $(C_1-C_4)$alkyl are methyl, ethyl, n-propyl, isopropyl, n-butyl, tert-butyl and sec-butyl radicals.

$(C_1-C_6)$alkoxy designates an —O—$(C_1-C_6)$alkyl radical.

Phenoxy designates an —O-phenyl radical.

Cycloalkyl group designates a cyclic, saturated hydrocarbon chain, having from 3 to 7 carbon atoms. Exemplary of a cycloalkyl group are cyclopropyl, cyclobutyl, cyclopentyl, cyclohexyl and cycloheptyl.

DETAILED DESCRIPTION OF BEST MODE AND SPECIFIC/PREFERRED EMBODIMENTS OF THE INVENTION

Preferred compounds of formula (I) defined above are those in which:

Y is C(O) or $CH_2$, $R_1$ is a $(C_1-C_4)$alkyl radical, $R_2$ is a hydrogen, fluorine, chlorine or bromine atom or a $(C_1-C_4)$alkyl radical, $R_3$ is a hydrogen atom, a $(C_1-C_4)$alkyl radical, or a —$WNR_6R_7$ radical wherein W is C(O), C(S) or $CH_2$, $R_6$ is a hydrogen atom or a $(C_1-C_4)$alkyl radical and $R_7$ is a cycloalkyl radical having 5, 6 or 7 carbon atoms or a phenyl radical, $R_4$ and $R'_4$ are identical and are each a $(C_1-C_4)$alkyl radical or else $R_4$ and $R'_4$ are bonded to one another and together form, with the carbon atom from which they depend, a cycloalkyl group having 5, 6 or 7 carbon atoms, $R_5$ is a group selected from among:

(i) an unsubstituted phenyl radical or phenyl substituted by one, two or three identical or different substituents selected from among the atoms fluorine, chlorine and bromine and the radicals $(C_1-C_4)$alkyl, trifluoromethyl, hydroxymethyl, mono-, di- and trifluoromethoxy, $(C_1-C_4)$alkoxy, phenoxy, benzyloxy, phenyl, 2-pyridyl, 3-pyridyl and 4-pyridyl, (ii) a $(C_2-C_{12})$alkyl radical, optionally substituted by one or more hydroxyl groups or fluorine atoms, (iii) a cycloalkyl radical or a —$CH_2$-cycloalkyl radical, (iv) an aralkyl radical —$(CH_2)_n$—Ar in which n is equal to 1, 2 or 3 and Ar is an unsubstituted phenyl radical or phenyl monosubstituted by a $(C_1-C_4)$alkyl, trifluoromethyl or $(C_1-C_4)$alkoxy radical, or a fluorine, chlorine or bromine atom, as well as their pharmaceutically acceptable salts, solvates or hydrates and their conformers or rotamers.

According to the present invention, among the compounds of formula (I) as defined above, particularly preferred compounds are those which have one or a combination of the following characteristics:

$R_1$ is a methyl, ethyl or isopropyl radical, $R_2$ is a chlorine or bromine atom or a methyl, ethyl, isopropyl or tert-butyl radical, $R_3$ is a hydrogen atom, a methyl radical or a —$WNR_6R_7$ radical wherein W is C(O), $R_6$ is a methyl radical and $R_7$ is a cyclohexyl radical or a phenyl radical, $R_4$ and $R'_4$ are identical and are each an ethyl or n-propyl radical, or else $R_4$ and $R'_4$ are bonded to one another and together form, with the carbon atom from which they depend, a cyclopentyl, cyclohexyl or cycloheptyl group, $R_5$ is a group selected from among:

(i) an unsubstituted phenyl radical or phenyl substituted by one, two or three identical or different substituents selected from among the atoms chlorine and fluorine, and the radicals methyl, ethyl, n-butyl, trifluoromethyl, hydroxymethyl, di- and trifluoromethoxy, methoxy, phenoxy and benzyloxy, (ii) a sec-butyl, n-propyl, n-butyl, n-pentyl, 2,2-dimethylpropyl, n-hexyl, n-heptyl, n-octyl, n-nonyl, an n-butyl radical substituted in position 4 by three fluorine atoms, an n-propyl radical substituted in position 3 by three fluorine atoms, an n-butyl radical substituted in position 4 by a hydroxyl radical, or an n-propyl group substituted in position 3 by a hydroxyl group, (iii) a —$CH_2$-cyclopropyl, —$CH_2$-cyclohexyl, cyclopentyl, cyclohexyl or cycloheptyl radical, (iv) a radical —$(CH_2)_n$—Ar with n equal to 1 or 2 and Ar is an unsubstituted phenyl radical or phenyl monosubstituted, preferably in the meta or para position, by a methyl, trifluoromethyl or methoxy radical or a fluorine atom.

According to the present invention, among the compounds of formula (I) as defined above, more particularly preferred compounds are those which have one or a combination of the following characteristics, when one does not exclude the other:

$R_1=R_2$=iPr, $R_3$=H;

$R_1=R_2$=Et, $R_3$=H;

$R_4$ and $R'_4$ are bonded to one another and together form, with the carbon atom from which they depend, a cyclopentyl or cyclohexyl group;

$R_5$ is an unsubstituted phenyl radical or phenyl substituted, in the meta or para position, by a chlorine or fluorine atom, or by a methyl or methoxy group;

Y=C(O).

The compounds below, as well as their pharmaceutically acceptable salts, solvates and hydrates and their conformers or rotamers are particularly preferred:

N-(2,6-Diisopropylphenyl)-2-(2,4-dioxo-1-phenyl-1,3-diazaspiro[4.4]non-3-yl)acetamide, compound (I.1) with Y=C(O); $R_1=R_2$=iPr; $R_3$=H; $R_4$ and $R'_4$ are bonded to one another to form a cyclopentyl; $R_5$=Ph

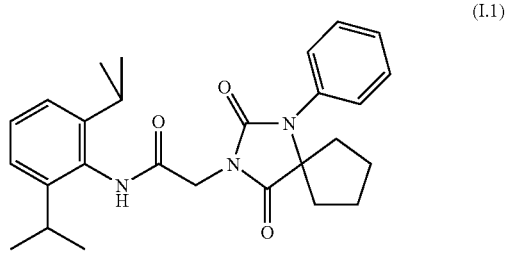

(I.1)

N-(2,6-Diisopropylphenyl)-2-(2,4-dioxo-1-phenyl-1,3-diazaspiro[4.5]dec-3-yl)acetamide, compound (I.2) with Y=C(O); $R_1=R_2$=iPr; $R_3$=H; $R_4$ and $R'_4$ are bonded to one another to form a cyclohexyl; $R_5$=Ph

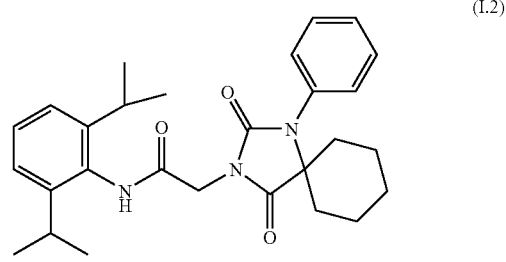

(I.2)

N-(Cyclohexyl)-4-[2-(2,4-dioxo-1-phenyl-1,3-diazaspiro[4.5]dec-3-yl]-acetylamino]-3,5,N-trimethylbenzamide, compound (I.3) with Y=C(O); $R_1$=$R_2$=Me; $R_3$=WNR$_6$R$_7$; $R_4$ and R'$_4$ are bonded to one another to form a cyclohexyl; $R_5$=Ph; $R_6$=Me; $R_7$=cyclohexyl; W=C(O)

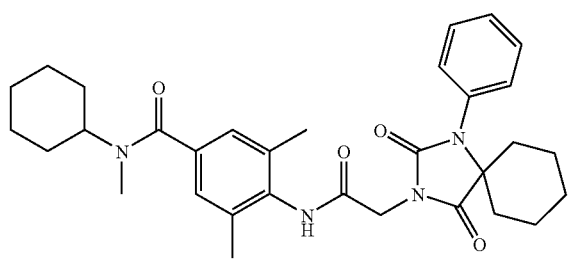

(I.3)

4-[2-(2,4-Dioxo-1-phenyl-1,3-diazaspiro[4.5]dec-3-y] acetylamino]-3,5,N-tri methyl-N-phenylbenzamide, compound (I.4) with Y=C(O); $R_1$=$R_2$=Me; $R_3$=WNR$_6$R$_7$; $R_4$ and R'$_4$ are bonded to one another to form a cyclohexyl; $R_5$=Ph, $R_6$=Me; $R_7$=Ph; W=C(O)

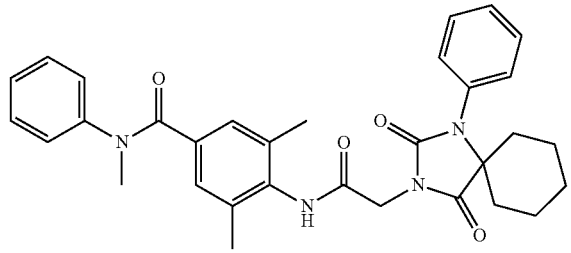

(I.4)

N-(2,6-Diisopropylphenyl)-2-(4-oxo-1-phenyl-1,3-diazaspiro[4.5]dec-3-yl)-acetamide, compound (I.5) with Y=CH$_2$; $R_1$=$R_2$=iPr; $R_3$=H; $R_4$ and R'$_4$ are bonded to one another to form a cyclohexyl; $R_5$=Ph

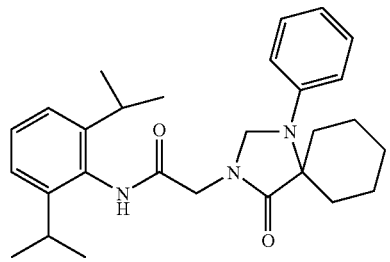

(I.5)

2-[1-(4-Chlorophenyl)-2,4-dioxo-1,3-diazaspiro[4.5]dec-3-yl]-N-(2,6-di-isopropylphenyl)acetamide, compound (I.6) with Y=C(O); $R_1$=$R_2$=iPr; $R_3$=H; $R_4$ and R'$_4$ are bonded to one another to form a cyclohexyl; $R_5$=4-Cl-Ph

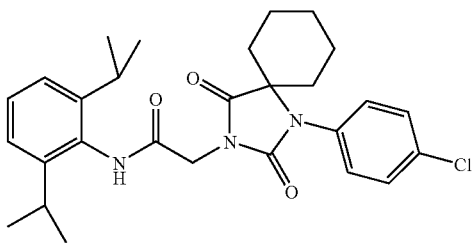

(I.6)

N-(2,6-Diisopropylphenyl)-2-[1-(4-fluorophenyl)-2,4-dioxo-1,3-diazaspiro-[4.5]dec-3-yl]acetamide, compound (I.7) with Y=C(O); $R_1$=$R_2$=iPr; $R_3$=H; $R_4$ and R'$_4$ are bonded to one another to form a cyclohexyl; $R_5$=4-F-Ph

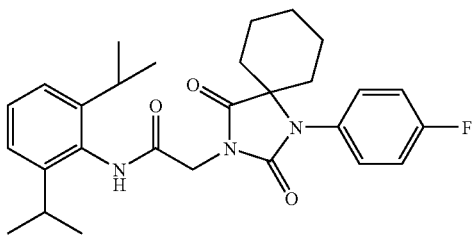

(I.7)

N-(2,6-Diisopropylphenyl)-2-[1-(4-methoxyphenyl)-2,4-dioxo-1,3-diazaspiro[4.5]dec-3-yl]acetamide, compound (I.8) with Y=C(O); $R_1$=$R_2$=iPr; $R_3$=H; $R_4$ and R'$_4$ are bonded to one another to form a cyclohexyl; $R_5$=4-MeO-Ph

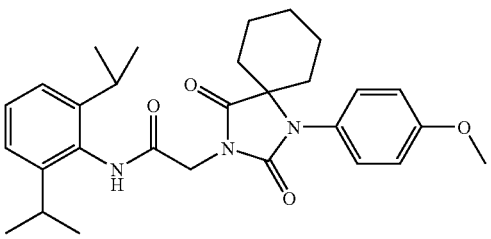

(I.8)

N-(2,6-Diisopropylphenyl)-2-(2,4-dioxo-1-phenyl-1,3-diazaspiro[4.6]undec-3-yl)acetamide, compound (I.9) with Y=C(O); $R_1$=$R_2$=iPr; $R_3$=H; $R_4$ and R'$_4$ are bonded to one another to form a cycloheptyl; $R_5$=Ph

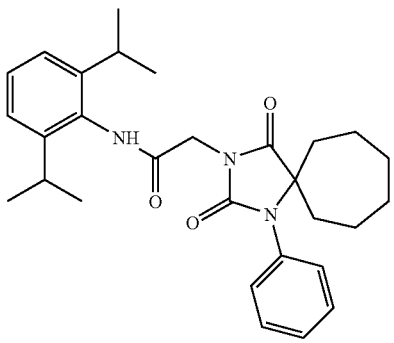

N-(2,6-Diisopropylphenyl)-2-(2,4-dioxo-1-p-tolyl-1,3-diazaspiro[4.5]dec-3-yl)acetamide, compound (I.10) with Y=C(O); $R_1=R_2=iPr$; $R_3=H$ $R_4$ and $R'_4$ are bonded to one another to form a cycloheptyl; $R_5$=4-Me-Ph

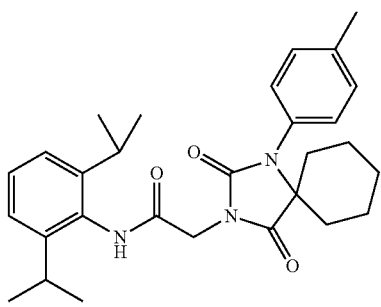

N-(2,6-Diisopropylphenyl)-2-[1-(3-fluorophenyl)-2,4-dioxo-1,3-diazaspiro[4.5]dec-3-yl]acetamide, compound (I.11) with Y=C(O); $R_1=R_2$ iPr; $R_3=H$; $R_4$ and $R'_4$ are bonded to one another to form a cyclohexyl; $R_5$=3-F-Ph

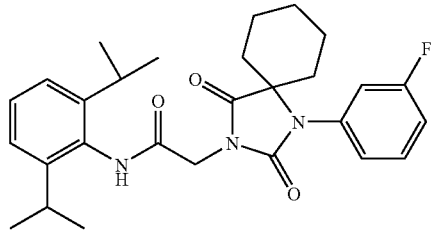

2-[1-(3-Chlorophenyl)-2,4-dioxo-1,3-diazaspiro[4.5]dec-3-yl]-N-(2,6-di-isopropylphenyl)acetamide, compound (I.12) with Y=C(O); $R_1=R_2=iPr$; $R_3=H$; $R_4$ and $R'_4$ are bonded to one another to form a cyclohexyl; $R_5$=3-Cl-Ph

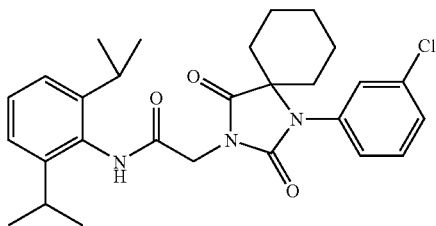

2-(1-Cyclopentyl-2,4-dioxo-1,3-diazaspiro[4.5]dec-3-yl)-N-(2,6-diisopropyl-phenyl)acetamide, compound (I.13) with Y=C(O); $R_1=R_2=iPr$; $R_3=H$; $R_4$ and $R'_4$ are bonded to one another to form a cyclohexyl; $R_5$=cyclopentyl

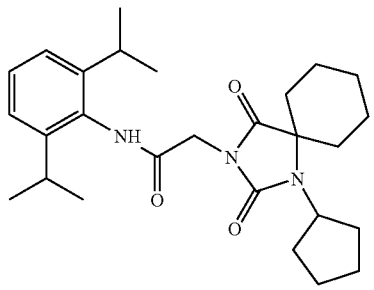

2-[1-Cyclohexyl-2,4-dioxo-1,3-diazaspiro[4.5]dec-3-yl)-N-(2,6-diisopropyl-phenyl)acetamide, compound (I.14) with Y=C(O); $R_1=R_2=iPr$; $R_3=H$; $R_4$ and $R'_4$ are bonded to one another to form a cyclohexyl; $R_5$=cyclohexyl

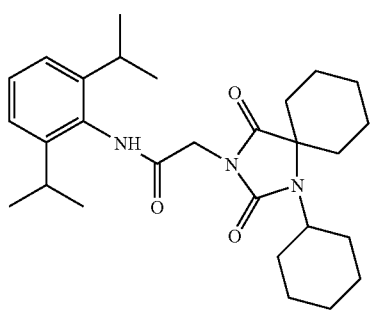

2-[1-(Cycloheptyl-2,4-dioxo-1,3-diazaspiro[4.5]dec-3-yl)-N-(2,6-di-isopropylphenyl)acetamide, compound (I.15) with Y=C(O); $R_1=R_2=iPr$; $R_3=H$; $R_4$ and $R'_4$ are bonded to one another to form a cyclohexyl; $R_5$=cycloheptyl

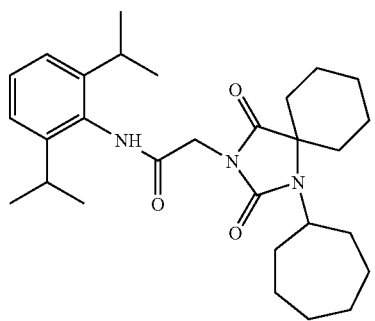

N-(2,6-Diisopropylphenyl)-2-(2,4-dioxo-1-m-tolyl-1,3-diazaspiro[4.5]dec-3-yl)acetamide, compound (I.16) with Y=C(O); $R_1=R_2$ iPr; $R_3$=H; $R_4$ and $R'_4$ are bonded to one another to form a cyclohexyl; $R_5$=3-Me-Ph

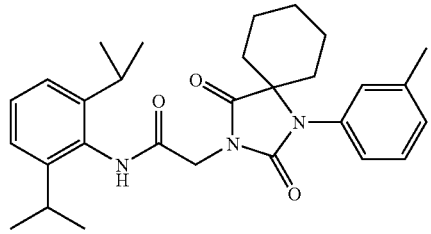

N-(2,6-Diisopropylphenyl)-2-[1-(4-fluorophenyl)-2,4-dioxo-1,3-diazaspiro[4.4]non-3-yl]acetamide, compound (I.17) with Y=C(O); $R_1=R_2$=iPr; $R_3$=H; $R_4$ and $R'_4$ are bonded to one another to form a cyclopentyl; $R_5$=4-F-Ph

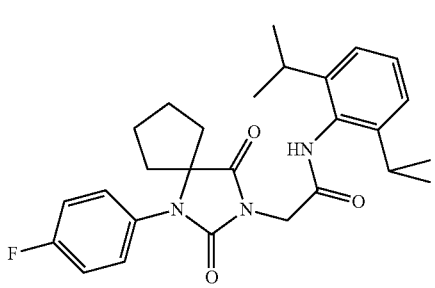

N-(2,6-Diisopropylphenyl)-2-[1-(3-methoxyphenyl)-2,4-dioxo-1,3-diazaspiro[4.5]dec-3-yl]acetamide, compound (I.18) with Y=C(O); $R_1=R_2$=iPr; $R_3$=H; $R_4$ and $R'_4$ are bonded to one another to form a cyclohexyl; $R_5$=3-MeO-Ph

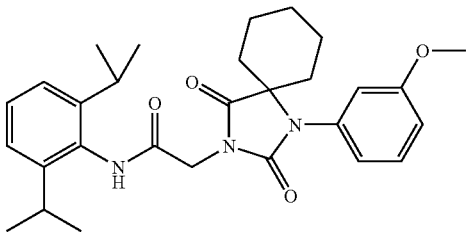

N-(2,6-Diisopropylphenyl)-2-[1-(2-fluorophenyl-2,4-dioxo-1,3-diazaspiro[4.5]dec-3-yl]acetamide, compound (I.19) with Y=C(O); $R_1=R_2$=iPr; $R_3$=H; $R_4$ and $R'_4$ are bonded to one another to form a cyclohexyl; $R_5$=2-F-Ph

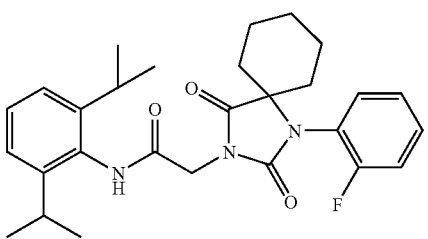

2-[1-(2-Chlorophenyl)-2,4-dioxo-1,3-diazaspiro[4.5]dec-3-yl]-N-(2,6-di-isopropylphenyl)acetamide, compound (I.20) with Y=C(O); $R_1=R_2$=iPr; $R_3$=H; $R_4$ and $R'_4$ are bonded to one another to form a cyclohexyl; $R_5$=2-Cl-Ph

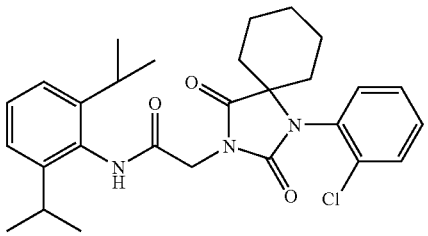

N-(2,6-Diisopropylphenyl)-2-(2,4-dioxo-1-o-tolyl-1,3-diazaspiro[4.5]dec-3-yl)acetamide, compound (I.21) with Y=C(O); $R_1=R_2$=iPr; R=H; $R_4$ and $R'_4$ are bonded to one another to form a cyclohexyl; $R_5$=2-Me-Ph

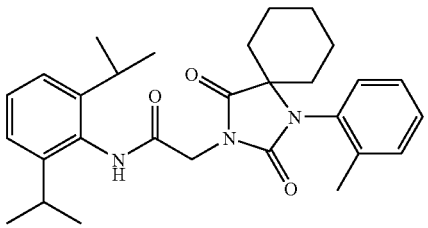

2-(1-Benzyl-2,4-dioxo-1,3-diazaspiro[4.5]dec-3-yl)-N-(2,6-diisopropyl-phenyl)acetamide, compound (I.22) with Y=C(O); $R_1=R_2$=iPr; $R_3$=H; $R_4$ and $R'_4$ are bonded to one another to form a cyclohexyl; $R_5$=(CH$_2$)$_n$—Ar; n=1; Ar=Ph

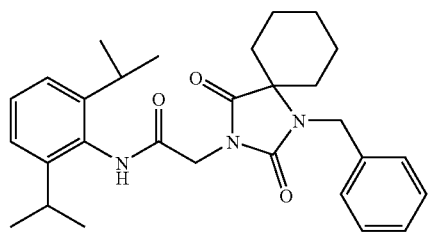

(I.22)

N-(2,6-Diisopropylphenyl)-2-(2,4-dioxo-1-phenethyl-1, 3-diazaspiro[4.5]dec-3-yl)acetamide, compound (I.23) with Y=C(O); $R_1=R_2$=iPr; $R_3$=H; $R_4$ and $R'_4$ are bonded to one another to form a cyclohexyl; $R_5$=(CH$_2$)$_n$—Ar; n=1; Ar=Ph

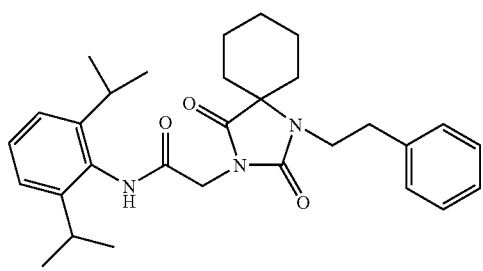

(I.23)

2-[1-(4-Chlorophenyl)-2,4-dioxo-1,3-diazaspiro[4.4]non-3-yl]-N-(2,6-di-isopropylphenyl)acetamide, compound (I.24) with Y=C(O); $R_1=R_2$=iPr; $R_3$=H; $R_4$ and $R'_4$ are bonded to one another to form a cyclopentyl; $R_5$=4-Cl-Ph

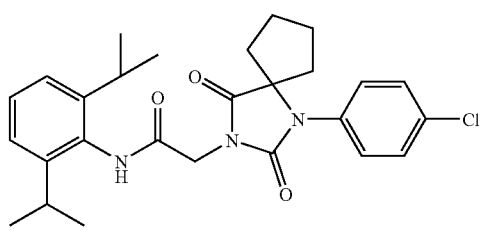

(I.24)

N-(2,6-Diisopropylphenyl)-2-(2,4-dioxo-1-propyl-1,3-diazaspiro[4.5]dec-3-yl)acetamide, compound (I.25) with Y=C(O); $R_1=R_2$=iPr; $R_3$=H; $R_4$ and $R'_4$ are bonded to one another to form a cyclohexyl; $R_5$=n-Pr

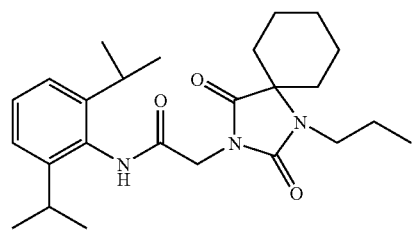

(I.25)

2-(1-Butyl-2,4-dioxo-1,3-diazaspiro[4.5]dec-3-yl)-N-(2, 6-diisopropylphenyl)acetamide, compound (I.26) with Y=C(O); $R_1=R_2$=iPr; $R_3$=H; $R_4$ and $R'_4$ are bonded to one another to form a cyclohexyl; $R_5$=n-Bu

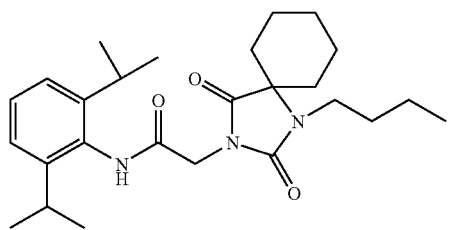

(I.26)

2-(1-Cyclohexylmethyl-2,4-dioxo-1,3-diazaspiro[4.5] dec-3-yl)-N-(2,6-di-isopropylphenyl)acetamide, compound (I.27) with Y=C(O); $R_1=R_2$=iPr; $R_3$=H; $R_4$ and $R'_4$ are bonded to one another to form a cyclohexyl; $R_5$=CH$_2$-cyclohexyl

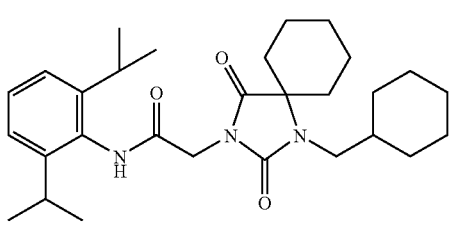

(I.27)

N-(2,6-Diisopropylphenyl)-2-(1-isobutyl-2,4-dioxo-1,3-diazaspiro[4.5]dec-3-yl)acetamide, compound (I.28) with Y=C(O); $R_1=R_2$=iPr; $R_3$=H; $R_4$ and $R'_4$ are bonded to one another to form a cyclohexyl; $R_5$=2-Me-Pr

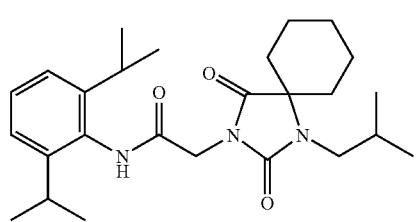

(I.28)

N-(2,6-Diisopropylphenyl)-2-(2,4-dioxo-1-pentyl-1,3-diazaspiro[4.5]dec-3-yl)acetamide, compound (I.29) with Y=C(O); $R_1=R_2$=iPr; $R_3$=H; $R_4$ and $R'_4$ are bonded to one another to form a cyclohexyl; $R_5$=n-pentyl

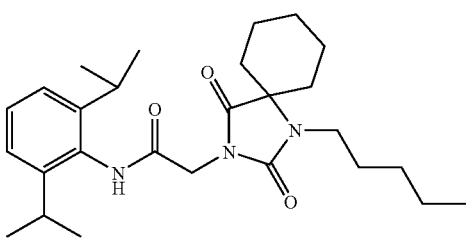

(I.29)

N-(2,6-Diisopropylphenyl)-2-(1-heptyl-2,4-dioxo-1,3-diazaspiro[4.5]dec-3-yl)acetamide, compound (I.30) with Y=C(O); $R_1=R_2$=iPr; $R_3$=H; $R_4$ and $R'_4$ are bonded to one another to form a cyclohexyl; $R_5$=n-heptyl (I.30)

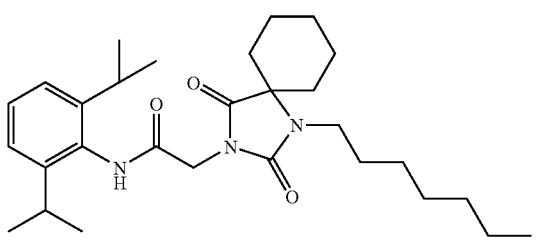

2-(1-Cyclopropylmethyl-2,4-dioxo-1,3-diazaspiro[4.5] dec-3-yl)-N-(2,6-di-isopropylphenyl)acetamide, compound (I.31) with Y=C(O); $R_1$=$R_2$=iPr; $R_3$=H; $R_4$ and $R'_4$ are bonded to one another to form a cyclohexyl; $R_5$=$CH_2$-cyclopropyl (I.31)

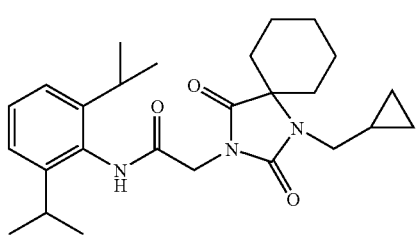

N-(2,6-Diisopropylphenyl)-2-[1-(2,2-dimethylpropyl)-2,4-dioxo-1,3-diazaspiro[4.5]dec-3-yl]acetamide, compound (I.32) with Y=C(O); $R_1$=$R_2$=iPr; $R_3$=H; $R_4$ and $R'_4$ are bonded to one another to form a cyclohexyl; $R_5$=2,2-dimethylpropyl (I.32)

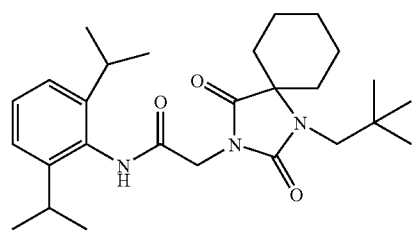

N-(2,6-Diisopropylphenyl)-2-[1-(2-methoxyphenyl)-2,4-dioxo-1,3-diazaspiro[4.5]dec-3-yl]acetamide, compound (I.33) with Y=C(O); $R_1$=$R_2$=iPr; $R_3$=H; $R_4$ and $R'_4$ are bonded to one another to form a cyclohexyl; $R_5$=2-MeO-Ph (I.33)

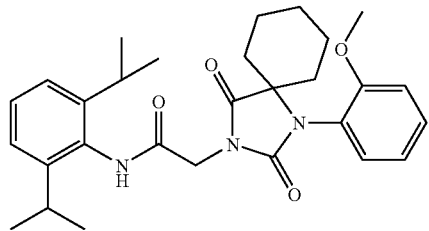

N-(2,6-Diisopropylphenyl)-2-(2,4-dioxo-1-p-tolyl-1,3-diazaspiro[4.4]non-3-yl)acetamide, compound (I.34) with Y=C(O); $R_1$=$R_2$=iPr; $R_3$=H; $R_4$ and $R'_4$ are bonded to one another to form a cyclopentyl; $R_5$=4-Me-Ph (I.34)

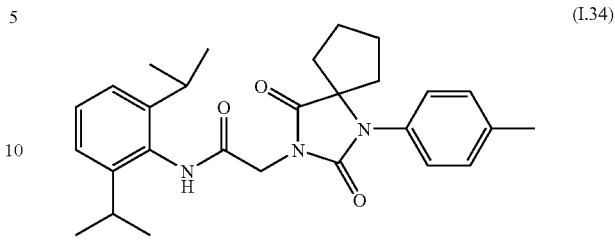

N-(2,6-Diisopropylphenyl)-2-(1-hexyl-2,4-dioxo-1,3-diazaspiro[4.5]dec-3-yl)acetamide, compound (I.35) with Y=C(O); $R_1$=$R_2$=iPr; $R_3$=H; $R_4$ and $R'_4$ are bonded to one another to form a cyclohexyl; $R_5$=n-hexyl (I.35)

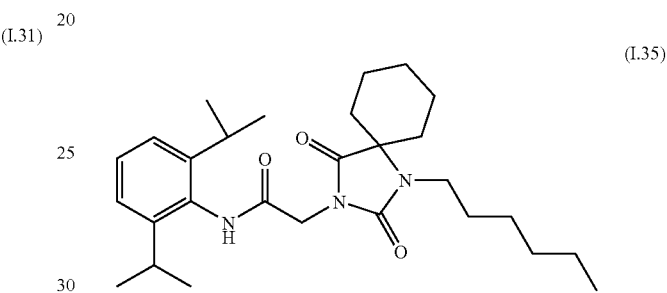

N-(2,6-Diisopropylphenyl)-2-[1-(4-ethylphenyl)-2,4-dioxo-1,3-diazaspiro[4.5]dec-3-yl]acetamide, compound (I.36) with Y=C(O); $R_1$=$R_2$=iPr; $R_3$=H; $R_4$ and $R'_4$ are bonded to one another to form a cyclohexyl; $R_5$=4-Et-Ph (I.36)

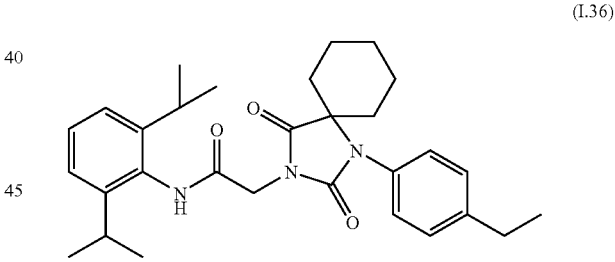

N-(2,6-Diisopropylphenyl)-2-[1-(4-ethylphenyl)-2,4-dioxo-1,3-diazaspiro[4.4]non-3-yl]acetamide, compound (I.37) with Y=C(O); $R_1$=$R_2$=iPr; $R_3$=H; $R_4$ and $R'_4$ are bonded to one another to form a cyclopentyl; $R_5$=4-Et-Ph (I.37)

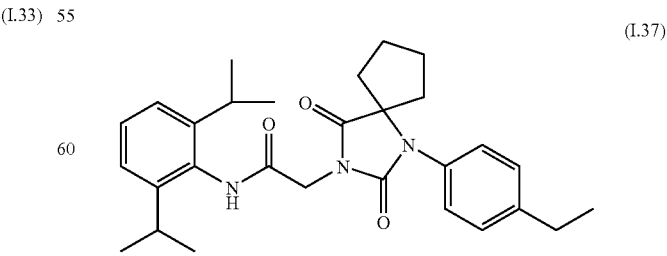

2-[1-(4-Butylphenyl)-2,4-dioxo-1,3-diazaspiro[4.5]dec-3-yl]-N-(2,6-diisopropylphenyl)acetamide, compound (I.38)

with Y=C(O); R$_1$=R$_2$=iPr; R$_3$=H; R$_4$ and R'$_4$ are bonded to one another to form a cyclohexyl; R$_5$=4-Bu-Ph

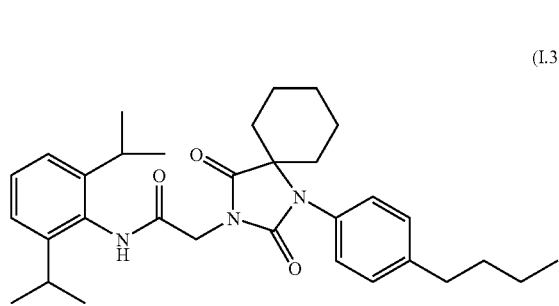
(I.38)

2-(4,4-Diethyl-2,5-dioxo-3-p-tolylimidazolidin-1-yl)-N-(2,6-diisopropylphenyl)acetamide, compound (I.39) with Y=C(O); R$_1$=R$_2$=iPr; R$_3$=H; R$_4$=R'$_4$=Et; R$_5$=4-Me-Ph

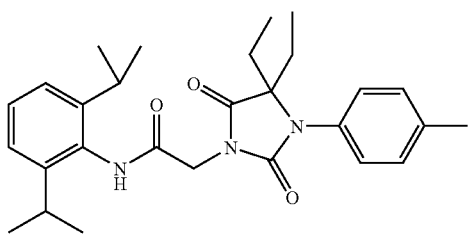
(I.39)

2-[1-(4-Butylphenyl)-2,4-dioxo-1,3-diazaspiro[4.4]non-3-yl]-N-(2,6-diisopropylphenyl)acetamide, compound (I.40) with Y=C(O); R$_1$=R$_2$=iPr; R$_3$=H; R$_4$ and R'$_4$ are bonded to one another to form a cyclopentyl; R$_5$=4-Bu-Ph

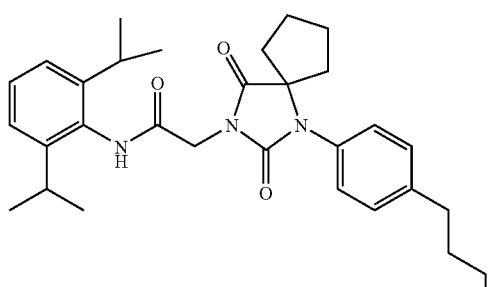
(I.40)

2-[1-(4-Benzyloxyphenyl)-2,4-dioxo-1,3-diazaspiro[4.4]non-3-yl]-N-(2,6-di-isopropylphenyl)acetamide, compound (I.41) with Y=C(O); R$_1$=R$_2$=iPr; R$_3$=H; R$_4$ and R'$_4$ are bonded to one another to form a cyclopentyl; R$_5$=4-BnO-Ph

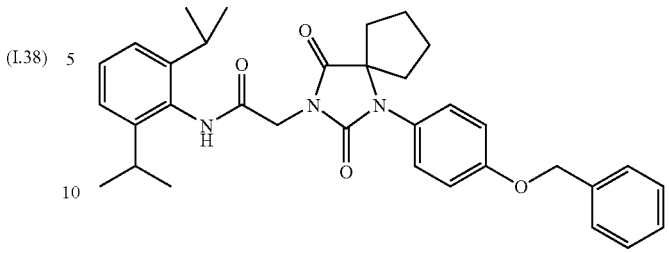
(I.41)

N-(2,6-Diisopropylphenyl)-2-[1-(4-hydroxymethylphenyl)-2,4-dioxo-1,3-diazaspiro[4.5]dec-3-yl]acetamide, compound (I.42) with Y=C(O); R$_1$=R$_2$=iPr; R$_3$=H; R$_4$ and R'$_4$ are bonded to one another to form a cyclohexyl; R$_5$=4-hydroxymethyl-Ph

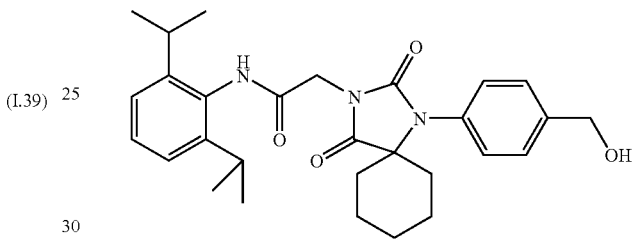
(I.42)

N-(2,6-Diisopropylphenyl)-2-(1-nonyl-2,4-dioxo-1,3-diazaspiro[4.5]dec-3-yl)acetamide, compound (I.43) with Y=C(O); R$_1$=R$_2$=iPr; R$_3$=H; R$_4$ and R'$_4$ are bonded to one another to form a cyclohexyl; R$_5$=n-nonyl

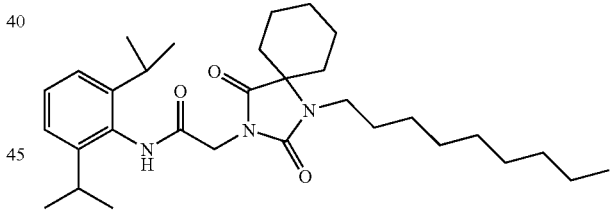
(I.43)

N-(2,6-Diisopropylphenyl)-2-(1-octyl-2,4-dioxo-1,3-diazaspiro[4.5]dec-3-yl)acetamide, compound (I.44) with Y=C(O); R$_1$=R$_2$=iPr; R$_3$=H; R$_4$ and R'$_4$ are bonded to one another to form a cyclohexyl; R$_5$=n-octyl (I.44)

2-(2,4-Dioxo-1-p-tolyl-1,3-diazaspiro[4.5]dec-3-yl)-N-(2,4,6-trimethylphenyl)acetamide, compound (I.45) with Y=C(O); $R_1$=$R_2$=$R_3$=Me; $R_4$ and $R'_4$ are bonded to one another to form a cyclohexyl; $R_5$=4-Me-Ph

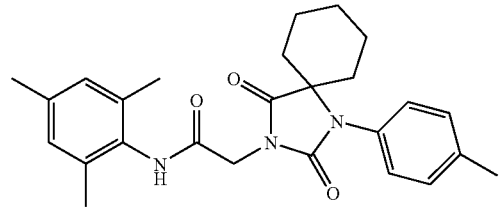
(I.45)

N-(2-Chloro-6-methylphenyl)-2-(2,4-dioxo-1-p-tolyl-1,3-diazaspiro[4.5]dec-3-yl)acetamide, compound (I.46) with Y=C(O); $R_1$=Me; =$R_2$=Cl; $R_3$=H; $R_4$ and $R'_4$ are bonded to one another to form a cyclohexyl; $R_5$=4-Me-Ph

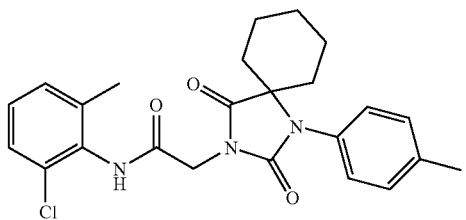
(I.46)

2-(2,4-Dioxo-1-p-tolyl-1,3-diazaspiro[4.5]dec-3-yl)-N-(2-isopropyl-6-methylphenyl)acetamide, compound (I.47) with Y=C(O); $R_1$=Me; $R_2$=iPr; $R_3$=H; $R_4$ and $R'_4$ are bonded to one another to form a cyclohexyl; $R_5$=4-Me-Ph

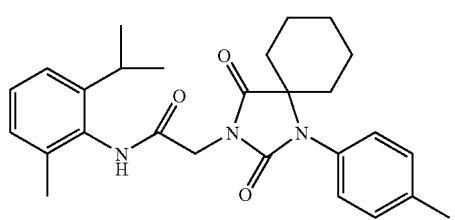
(I.47)

N-(2,6-Diethylphenyl)-2-(2,4-dioxo-1-p-tolyl-1,3-diazaspiro[4.5]dec-3-yl)-acetamide, compound (I.48) with Y=C(O); $R_1$=$R_2$=Et; $R_3$=H; $R_4$ and $R'_4$ are bonded to one another to form a cyclohexyl; $R_5$=4-Me-Ph

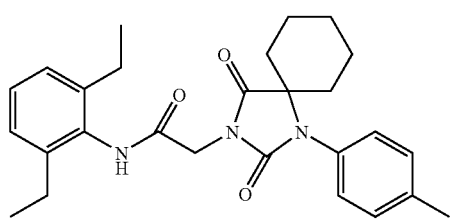
(I.48)

N-(2,6-Diethyl-4-methylphenyl)-2-(2,4-dioxo-1-p-tolyl-1,3-diazaspiro[4.5]dec-3-yl)acetamide, compound (I.49) with Y=C(O); $R_1$=$R_2$=Et; $R_3$=Me; $R_4$ and $R'_4$ are bonded to one another to form a cyclohexyl; $R_5$=4-Me-Ph

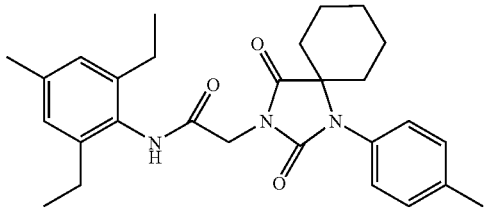
(I.49)

N-(2-Chloro-4,6-dimethylphenyl)-2-(2,4-dioxo-1-p-tolyl-1,3-diazaspiro[4.5]dec-3-yl)acetamide, compound (I.50) with Y=C(O); $R_1$=Me; $R_2$=Cl; $R_3$=Me; $R_4$ and $R'_4$ are bonded to one another to form a cyclohexyl; $R_5$=4-Me-Ph

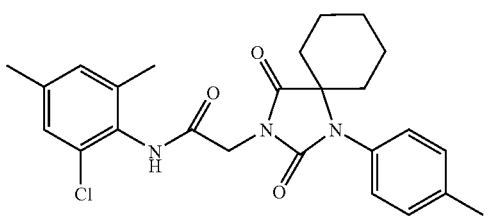
(I.50)

N-(2,6-Diethylphenyl)-2-(2,4-dioxo-1-phenethyl-1,3-diazaspiro[4.5]dec-3-yl)acetamide, compound (I.51) with Y=C(O); $R_1$=$R_2$=Et; $R_3$=H; $R_4$ and $R'_4$ are bonded to one another to form a cyclohexyl; $R_5$=$(CH_2)_n$—Ar; n=2; Ar=Ph

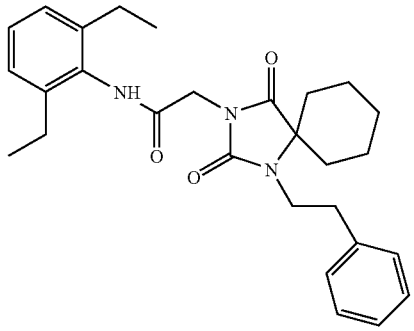
(I.51)

N-(2-Bromo-4,6-dimethylphenyl)-2-(2,4-dioxo-1-p-tolyl-1,3-diazaspiro[4.5]dec-3-yl)acetamide, compound (I.52) with Y=C(O); $R_1$=Me; $R_2$=Br; $R_3$=Me; $R_4$ and $R'_4$ are bonded to one another to form a cyclohexyl; $R_5$=4-Me-Ph

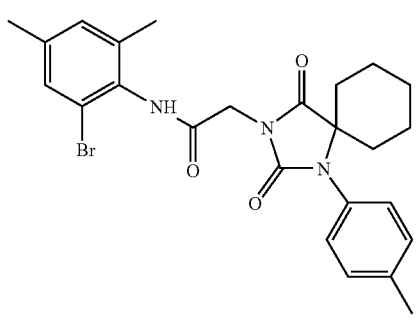

(I.52)

N-(2-tert-Butyl-6-methylphenyl)-2-(2,4-dioxo-1-p-tolyl-1,3-diazaspiro[4.5]dec-3-yl)acetamide, compound (I.53) with Y=C(O); $R_1$=Me; $R_2$=tBu; $R_3$=H; $R_4$ and $R'_4$ are bonded to one another to form a cyclohexyl; $R_5$=4-Me-Ph

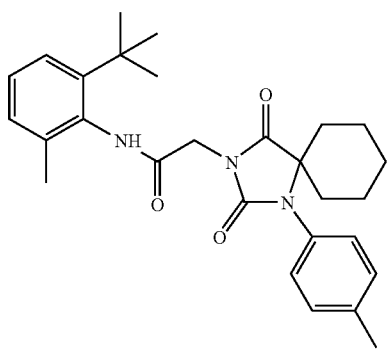

(I.53)

N-(2,6-Diethylphenyl)-2-[1-(4-ethylphenyl)-2,4-dioxo-1,3-diazaspiro[4.5]dec-3-yl]acetamide, compound (I.54) with Y=C(O); $R_1$=$R_2$=Et; $R_3$=H; $R_4$ and $R'_4$ are bonded to one another to form a cyclohexyl; $R_5$=4-Et-Ph

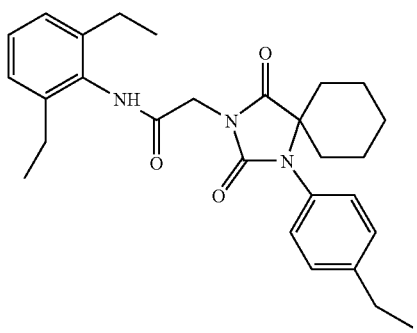

(I.54)

N-(2,6-Diethylphenyl)-2-(2,4-dioxo-1-propyl-1,3-diazaspiro[4.5]dec-3-yl)acetamide, compound (I.55) with Y=C(O); $R_1$=$R_2$=Et; $R_3$=H; $R_4$ and $R'_4$ are bonded to one another to form a cyclohexyl; $R_5$=n-Pr

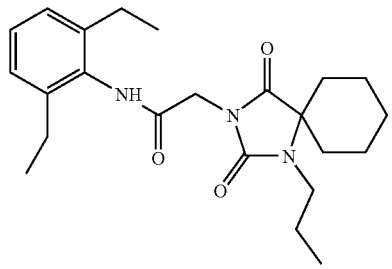

(I.55)

2-[1-(4-Butylphenyl)-2,4-dioxo-1,3-diazaspiro[4.5]dec-3-yl]-N-(2,6-diethyl-phenyl)acetamide, compound (I.56) with Y=C(O); $R_1$=$R_2$=Et; $R_3$=H; $R_4$ and $R'_4$ are bonded to one another to form a cyclohexyl; $R_5$=4-Bu-Ph

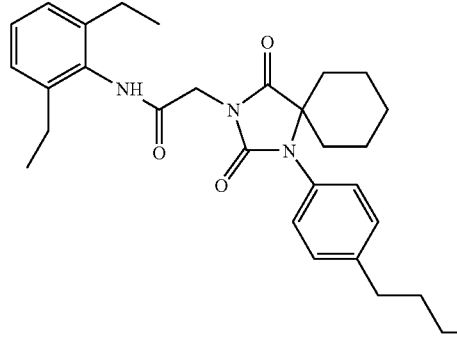

(I.56)

N-(2,6-Diethylphenyl)-2-[1-(4-ethylphenyl)-2,4-dioxo-1,3-diazaspiro[4.4]non-3-yl]acetamide, compound (I.57) with Y=C(O); $R_1$=$R_2$=Et; $R_3$=H; $R_4$ and $R'_4$ are bonded to one another to form a cyclopentyl; $R_5$=4-Et-Ph

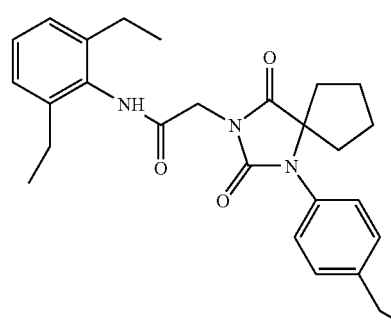

(I.57)

N-(2,6-Diethylphenyl)-2-(1-heptyl-2,4-dioxo-1,3-diazaspiro[4.5]dec-3-yl)acetamide, compound (I.58) with Y=C(O); $R_1$=$R_2$=Et; $R_3$=H; $R_4$ and $R'_4$ are bonded to one another to form a cyclohexyl; $R_5$=n-heptyl

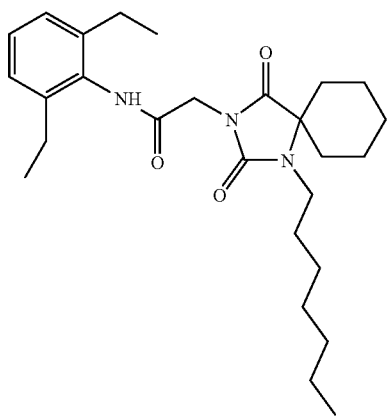

N-(2,6-Diethylphenyl)-2-(1-isobutyl-2,4-dioxo-1,3-diazaspiro[4.5]dec-3-yl)acetamide, compound (I.59) with Y=C(O); R₁=R₂=Et; R₃=H; R₄ and R'₄ are bonded to one another to form a cyclohexyl; R₅=2-Me-Pr

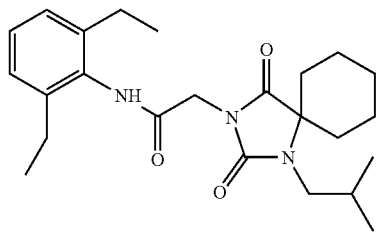

2-[1-(4-Benzyloxyphenyl)-2,4-dioxo-1,3-diazaspiro[4.5]dec-3-yl]-N-(2,6-di-isopropylphenyl)acetamide, compound (I.60) with Y=C(O); R₁=R₂=iPr; R₃=H; R₄ and R'₄ are bonded to one another to form a cyclohexyl; R₅=4-BnO-Ph

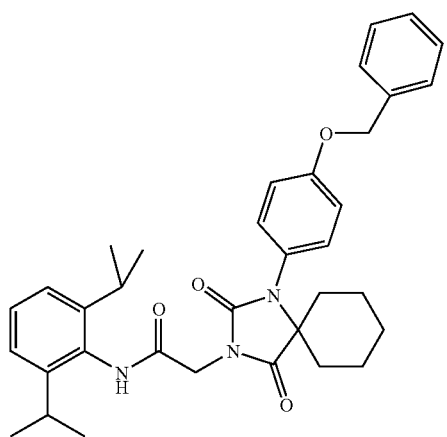

2-[1-(4-Chlorophenyl)-2,4-dioxo-1,3-diazaspiro[4.4]non-3-yl]-N-(2,6-diethylphenyl)acetamide, compound (I.61) with Y=C(O); R₁=R₂=Et; R₃=H; R₄ and R'₄ are bonded to one another to form a cyclopentyl; R₅=4-Cl-Ph

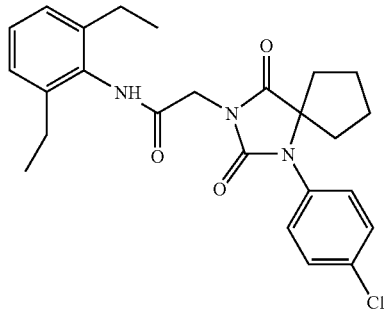

2-[1-(4-Benzyloxyphenyl)-2,4-dioxo-1,3-diazaspiro[4.5]dec-3-yl]-N-(2,6-di-ethylphenyl)acetamide, compound (I.62) with Y=C(O); R₁=R₂=Et; R₃=H; R₄ and R'₄ are bonded to one another to form a cyclohexyl; R₅=4-BnO-Ph

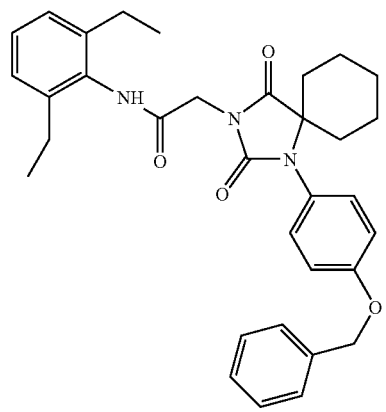

2-(1-Benzyl-2,4-dioxo-1,3-diazaspiro[4.5]dec-3-yl)-N-(2,6-diethylphenyl)-acetamide, compound (I.63) with Y=C(O); R₁=R₂=Et; R₃=H; R₄ and R'₄ are bonded to one another to form a cyclohexyl; R₅=(CH₂)ₙ—Ar; n=1; Ar=Ph

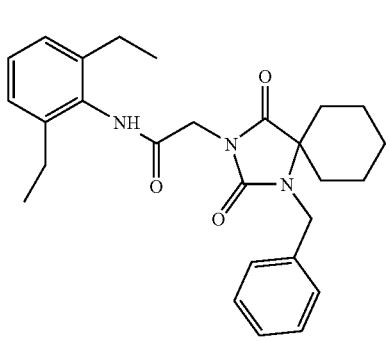

N-(2,6-Diisopropylphenyl)-2-[2,4-dioxo-1-(4-trifluoromethylphenyl)-1,3-diazaspiro[4.5]dec-3-yl]acetamide, compound (I.64) with Y=C(O); R₁=R₂=iPr; R₃=H; R₄ and R'₄ are bonded to one another to form a cyclohexyl; R₅=4-CF₃-Ph

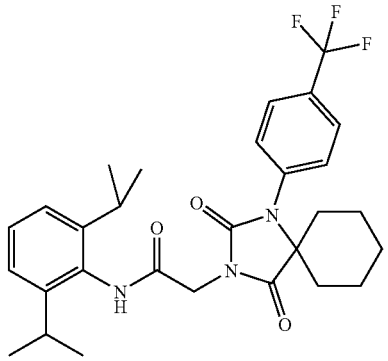

(I.64)

N-(2,6-Diisopropylphenyl)-2-[2,4-dioxo-1-(3-trifluoromethylphenyl)-1,3-diazaspiro[4.5]dec-3-yl]acetamide, compound (I.65) with Y=C(O); R₁=R₂=iPr; R₃=H; R₄ and R'₄ are bonded to one another to form a cyclohexyl; R₅=3-CF₃-Ph

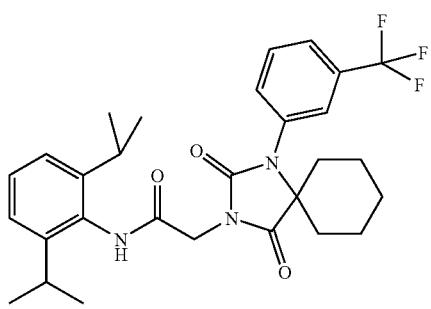

(I.65)

N-(2,6-Diisopropylphenyl)-2-[2,4-dioxo-1-(2-trifluoromethylphenyl)-1,3-diazaspiro[4.5]dec-3-yl]acetamide, compound (I.66) with Y=C(O); R₁=R₂=iPr; R₃=H; R₄ and R'₄ are bonded to one another to form a cyclohexyl; R₅=2-CF₃-Ph

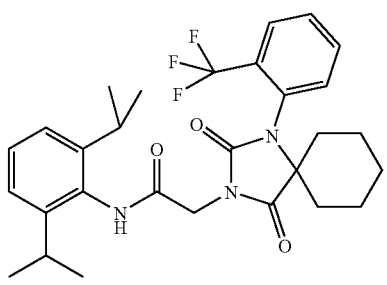

(I.66)

2-[1-(4-Difluoromethoxyphenyl)-2,4-dioxo-1,3-diazaspiro[4.5]dec-3-yl]-N-(2,6-diisopropylphenyl)acetamide, compound (I.67) with Y=C(O); R₁=R₂=iPr; R₃=H; R₄ and R'₄ are bonded to one another to form a cyclohexyl; R₅=4-CHF₂O-Ph

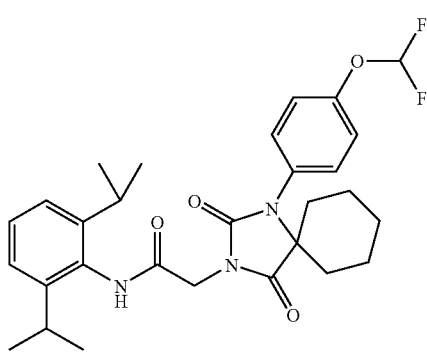

(I.67)

2-[1-(4-Trifluoromethoxyphenyl)-2,4-dioxo-1,3-diazaspiro[4.5]dec-3-yl]-N-(2,6-diisopropyl-phenyl)acetamide, compound (I.68) with Y=C(O); R₁=R₂=iPr; R₃=H; R₄ and R'₄ are bonded to one another to form a cyclohexyl; R₅=4-CF₃O-Ph

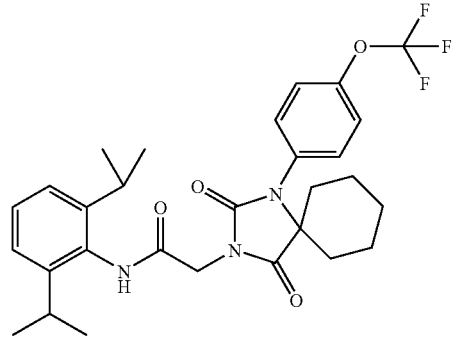

(I.68)

N-(2,6-Diisopropylphenyl)-2-[1-(3,4-dimethylphenyl)-2,4-dioxo-1,3-diazaspiro[4.5]dec-3-yl]acetamide, compound (I.69) with Y=C(O); R₁=R₂=iPr; R₃=H; R₄ and R'₄ are bonded to one another to form a cyclohexyl; R₅=3,4-diMe-Ph

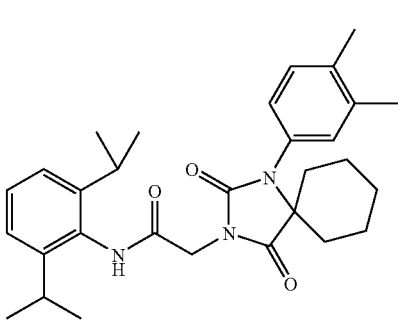

(I.69)

N-(2,6-Diisopropylphenyl)-2-[1-(2,4-dimethylphenyl)-2,4-dioxo-1,3-diazaspiro[4.5]dec-3-yl]acetamide, compound (I.70) with Y=C(O); R₁=R₂ iPr; R₃=H; R₄ and R'₄ are bonded to one another to form a cyclohexyl; R₅=2,4-diMe-Ph

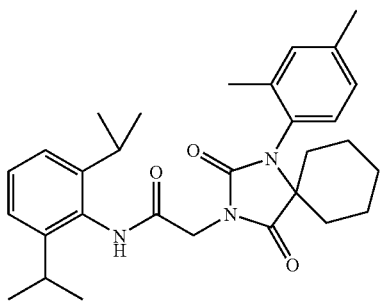

(I.70)

N-(2,6-Diisopropylphenyl)-2-[1-(3-fluoro-4-methylphenyl)-2,4-dioxo-1,3-diazaspiro[4.5]dec-3-yl]acetamide, compound (I.71) with Y=C(O); $R_1$=$R_2$=iPr; $R_3$=H; $R_4$ and $R'_4$ are bonded to one another to form a cyclohexyl; $R_5$=3-F-4-Me-Ph

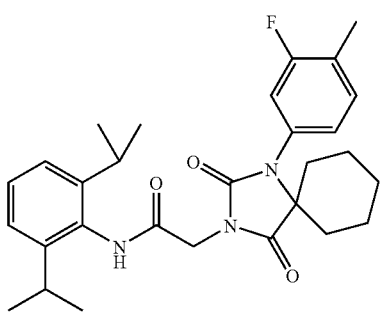

(I.71)

N-(2,6-Diisopropylphenyl)-2-[1-(4-methyl-3-trifluoromethylphenyl)-2,4-dioxo-1,3-diazaspiro[4.5]dec-3-yl]acetamide, compound (I.72) with Y=C(O); $R_1$=$R_2$=iPr; $R_3$=H; $R_4$ and $R'_4$ are bonded to one another to form a cyclohexyl; $R_5$=4-Me-3-CF$_3$-Ph

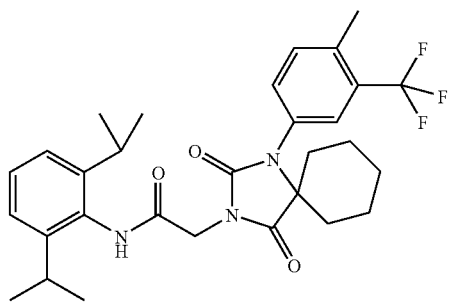

(I.72)

N-(2,6-Diisopropylphenyl)-2-[1-(3,5-difluoro-4-methylphenyl)-2,4-dioxo-1,3-diazaspiro[4.5]dec-3-yl]acetamide, compound (I.73) with Y=C(O); $R_1$=$R_2$=iPr; $R_3$=H; $R_4$ and $R'_4$ are bonded to one another to form a cyclohexyl; $R_5$=3,5-diF-4-Me-Ph

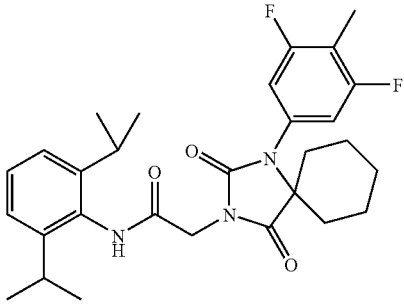

(I.73)

N-(2,6-Diisopropylphenyl)-2-[1-(2-fluoro-4-methylphenyl)-2,4-dioxo-1,3-diazaspiro[4.5]dec-3-yl]acetamide, compound (I.74) with Y=C(O); $R_1$=$R_2$=iPr; $R_3$=H; $R_4$ and $R'_4$ are bonded to one another to form a cyclohexyl; $R_5$=2-F-4-Me-Ph

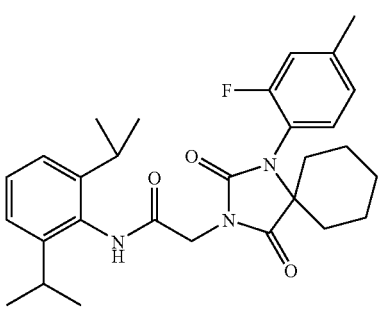

(I.74)

N-(2,6-Diisopropylphenyl)-2-[1-(4-fluoro-3-methylphenyl)-2,4-dioxo-1,3-diazaspiro[4.5]dec-3-yl]acetamide, compound (I.75) with Y=C(O); $R_1$=$R_2$=iPr; $R_3$=H; $R_4$ and $R'_4$ are bonded to one another to form a cyclohexyl; $R_5$=4-F-3-Me-Ph

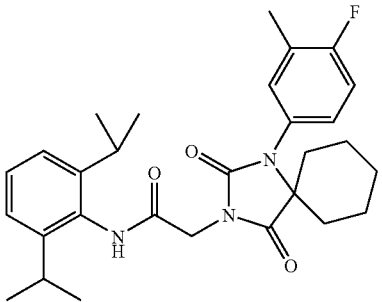

(I.75)

N-(2,6-Diisopropylphenyl)-2-[1-(4-chloro-3-methylphenyl)-2,4-dioxo-1,3-diazaspiro[4.5]dec-3-yl]acetamide, compound (I.76) with Y=C(O); $R_1$=$R_2$=iPr; $R_3$=H; $R_4$ and $R'_4$ are bonded to one another to form a cyclohexyl; $R_5$=4-Cl-3-Me-Ph

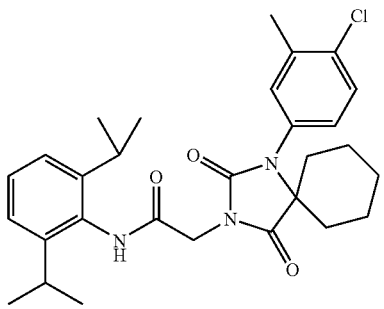
(I.76)

N-(2,6-Diisopropylphenyl)-2-[2,4-dioxo-1-(3-phenoxyphenyl)-1,3-diazaspiro[4.5]dec-3-yl]acetamide, compound (I.77) with Y=C(O); R₁=R₂=iPr; R₃=H; R₄ and R'₄ are bonded to one another to form a cyclohexyl; R₅=4-PhO-Ph

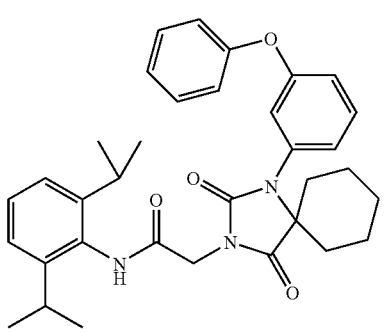
(I.77)

N-(2,6-Diisopropylphenyl)-2-(2,5-dioxo-4,4-dipropyl-3-p-tolylimidazolidin-1-yl)acetamide, compound (I.78) with Y=C(O); R₁=R₂=iPr; R₃=H; R₄=R'₄=nPr; R₅=4-Me-Ph

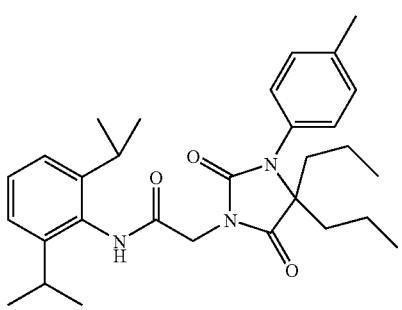
(I.78)

2-(4,4-Dibutyl-2,5-dioxo-3-p-tolylimidazolidin-1-yl)-N-(2,6-diisopropyl-phenyl)acetamide, compound (I.79) with Y=C(O); R₁=R₂=iPr; R₃=H; R₄=R'₄=nBu; R₅=4-Me-Ph

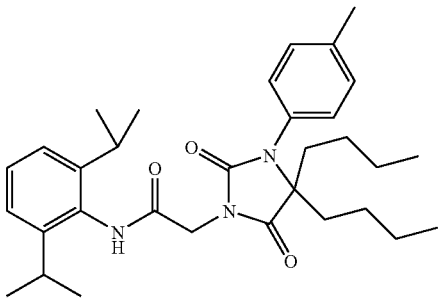
(I.79)

N-(2,6-Diisopropylphenyl)-2-[2,4-dioxo-1-(4,4,4-trifluorobutyl)-1,3-diazaspiro[4.5]dec-3-yl]acetamide, compound (I.80) with Y=C(O); R₁=R₂=iPr; R₃=H; R₄ and R'₄ are bonded to one another to form a cyclohexyl; R₅=4,4,4-FFF-nBu

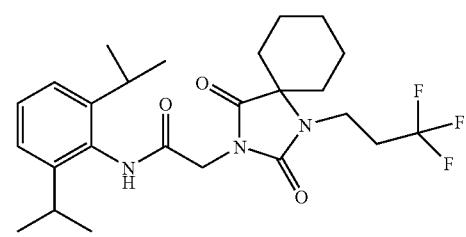
(I.80)

N-(2,6-Diisopropylphenyl)-2-[2,4-dioxo-1-(4,4,4-trifluoropropyl)-1,3-diazaspiro[4.5]dec-3-yl]acetamide, compound (I.81) with Y=C(O); R₁=R₂ iPr; R₃=H; R₄ and R'₄ are bonded to one another to form a cyclohexyl; R₅=3,3,3-FFF-nPr (I.81)

N-(2,6-Diisopropylphenyl)-2-[1-(3-hydroxypropyl)-2,4-dioxo-1,3-diazaspiro[4.5]dec-3-yl]acetamide, compound (I.82) with Y=C(O); R₁=R₂ iPr; R₃=H; R₄ and R'₄ are bonded to one another to form a cyclohexyl; R₅=3-OH-nPr

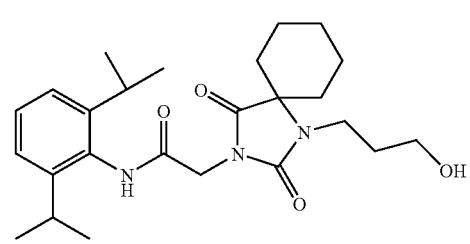
(I.82)

N-(2,6-Diisopropylphenyl)-2-[1-(3-hydroxybutyl)-2,4-dioxo-1,3-diazaspiro[4.5]dec-3-yl]acetamide, compound (I.83) with Y=C(O); $R_1$=$R_2$=iPr; $R_3$=H; $R_4$ and $R'_4$ are bonded to one another to form a cyclohexyl; $R_5$=4-OH-nBu (I.83)

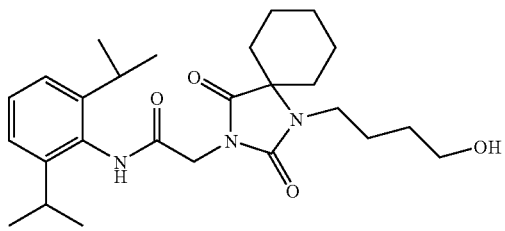

N-(2,6-Diisopropylphenyl)-2-[1-(4-fluorobenzyl)-2,4-dioxo-1,3-diazaspiro[4.5]dec-3-yl]acetamide, compound (I.84) with Y=C(O); $R_1$=$R_2$=iPr; $R_3$=H; $R_4$ and $R'_4$ are bonded to one another to form a cyclohexyl; $R_5$=$(CH_2)_n$—Ar; n=1; Ar=4F-Ph (I.84)

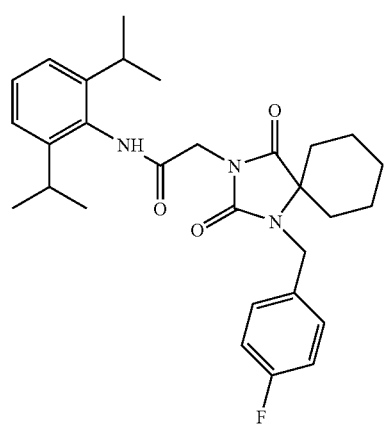

N-(2,6-Diisopropylphenyl)-2-[1-(4-methylbenzyl)-2,4-dioxo-1,3-diazaspiro[4.5]dec-3-yl]acetamide, compound (I.85) with Y=C(O); $R_1$=$R_2$=iPr; $R_3$=H; $R_4$ and $R'_4$ are bonded to one another to form a cyclohexyl; $R_5$=$(CH_2)_n$—Ar; n=1; Ar=4Me-Ph (I.85)

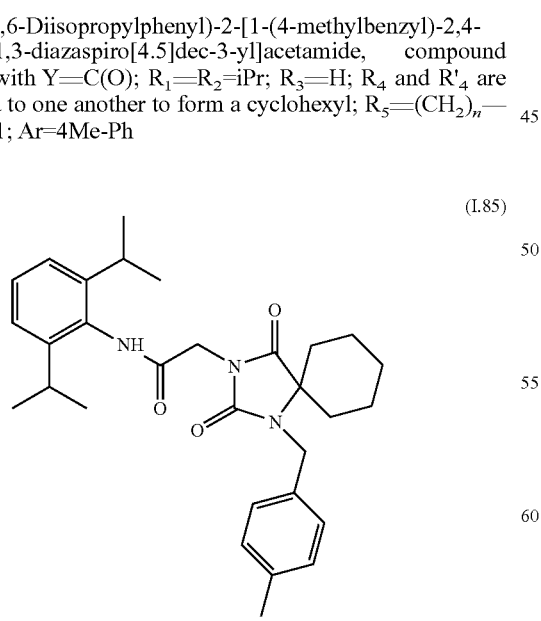

N-(2,6-Diisopropylphenyl)-2-[2,4-dioxo-1-(4-trifluoromethylbenzyl)-1,3-diazaspiro[4.5]dec-3-yl]acetamide, compound (I.86) with Y=C(O); $R_1$=$R_2$=iPr; $R_3$=H; $R_4$ and $R'_4$ are bonded to one another to form a cyclohexyl; $R_5$=$(CH_2)_n$—Ar; n=1; 4CF$_3$-Ph (I.86)

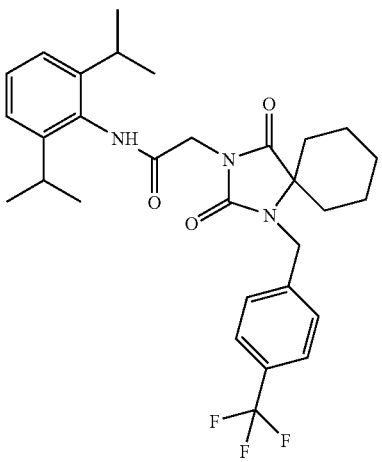

N-(2,6-Diisopropylphenyl)-2-[1-(3-methylbenzyl)-2,4-dioxo-1,3-diazaspiro[4.5]dec-3-yl]acetamide, compound (I.87) with Y=C(O); $R_1$=$R_2$=iPr; $R_3$=H; $R_4$ and $R'_4$ are bonded to one another to form a cyclohexyl; $R_5$=$(CH_2)_n$—Ar; n=1; Ar=3Me-Ph (I.87)

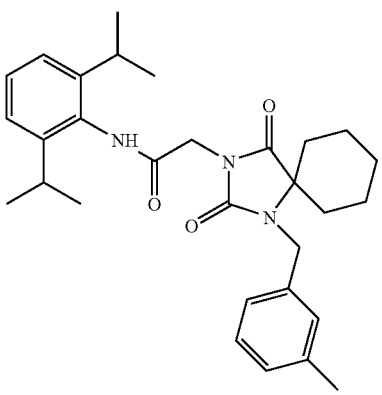

N-(2,6-Diisopropylphenyl)-2-[1-(3-fluorobenzyl)-2,4-dioxo-1,3-diazaspiro[4.5]dec-3-yl]acetamide, compound (I.88) with Y=C(O); $R_1$=$R_2$=iPr; $R_3$=H; $R_4$ and $R'_4$ are bonded to one another to form a cyclohexyl; $R_5$=$(CH_2)_n$—Ar; n=1; Ar=3F-Ph (I.88)

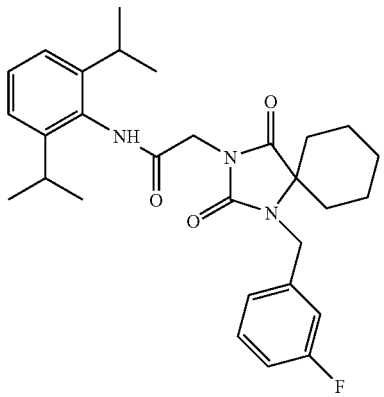

N-(2,6-Diisopropylphenyl)-2-[1-(3-methoxybenzyl)-2,4-dioxo-1,3-diazaspiro[4.5]dec-3-yl]acetamide, compound (I.89) with Y=C(O); $R_1=R_2$=iPr; $R_3$=H; $R_4$ and $R'_4$ are bonded to one another to form a cyclohexyl; $R_5$=(CH$_2$)$_n$—Ar; n=1; Ar=3MeO-Ph (I.89)

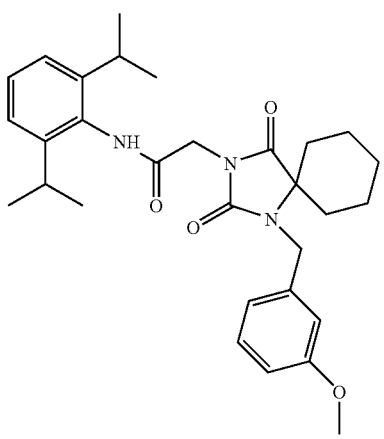

N-(2,6-Diisopropylphenyl)-2-[2,4-dioxo-1-(3-trifluoromethylbenzyl)-1,3-diazaspiro[4.5]dec-3-yl]acetamide, compound (I.90) with Y=C(O); $R_1=R_2$=iPr; $R_3$=H; $R_4$ and $R'_4$ are bonded to one another to form a cyclohexyl; $R_5$=(CH$_2$)$_n$—Ar; n=1; Ar=3CF$_3$-Ph (I.90)

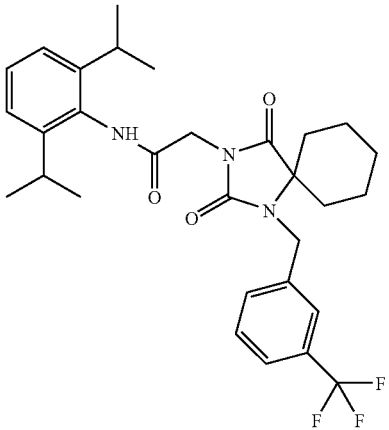

N-(2,6-Diisopropylphenyl)-2-[1-(2-methylbenzyl)-2,4-dioxo-1,3-diazaspiro[4.5]dec-3-yl]acetamide, compound (I.91) with Y=C(O); $R_1=R_2$=iPr; $R_3$=H; $R_4$ and $R'_4$ are bonded to one another to form a cyclohexyl; $R_5$=(CH$_2$)$_n$—Ar; n=1; Ar=2-Me-Ph (I.91)

N-(2,6-Diisopropylphenyl)-2-[1-(2-fluorobenzyl)-2,4-dioxo-1,3-diazaspiro[4.5]dec-3-yl]acetamide, compound (I.92) with Y=C(O); $R_1=R_2$=iPr; $R_3$=H; $R_4$ and $R'_4$ are bonded to one another to form a cyclohexyl; $R_5$=(CH$_2$)$_n$—Ar; n=1; Ar=2F-Ph (I.92)

N-(2,6-Diisopropylphenyl)-2-[2,4-dioxo-1-(2-trifluoromethylbenzyl)-1,3-diazaspiro[4.5]dec-3-yl]acetamide compound (I.93) with Y=C(O); $R_1=R_2=iPr$; $R_3=H$; $R_4$ and $R'_4$ are bonded to one another to form a cyclohexyl; $R_5=(CH_2)_n$—Ar; n=1; Ar=3CF$_3$-Ph

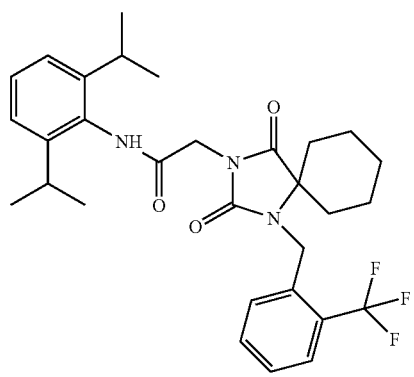

(I.93)

The salts of the compounds according to the invention are prepared according to techniques well known to one skilled in the art. The salts of the compounds of formula (I) according to the present invention comprise those with inorganic or organic acids which allow a suitable separation or a crystallization of the compounds of formula (I), as well as pharmaceutically acceptable salts. As an appropriate acid, it is possible to mention: picric acid, oxalic acid or an optically active acid, for example a tartaric acid, a dibenzoyltartaric acid, a mandelic acid or a camphorsulfonic acid, and those which form physiologically acceptable salts, such as the hydrochloride, the hydrobromide, the sulfate, the hydrogensulfate, the dihydrogenphosphate, the maleate, the fumarate, the 2-naphthalenesulfonate and the para-toluenesulfonate, the hydrochloride being preferred.

The solvates or hydrates may be obtained directly from the synthesis process, the compound (I) being isolated in the form of a hydrate, for example a mono- or hemihydrate or a solvate of the reaction or purification solvent.

The compounds of formula (I) can be purified according to any conventional purification technique, for example by crystallization or purification by column chromatography.

When a compound of formula (I) according to the invention has one or more asymmetric carbons, the optical isomers of this compound are integral parts of the present invention. The compounds of formula (I) can thus be found in the form of a pure isomer or of a mixture of isomers in any proportion.

"Conformers" are understood as meaning an element of a set of conformational stereoiomers of which each is characterized by a conformation corresponding to a distinct minimum potential energy of the molecular entity.

"Rotamer" means an element of an assembly of conformers resulting from a restricted rotation around a single bond.

The compounds of formula (I) according to the invention can be prepared according to SCHEME 1 below, in which Y, $R_1$, $R_2$, $R_3$, $R_4$, $R_4'$ and $R_5$ are as defined for the compounds of formula (I):

SCHEME 1

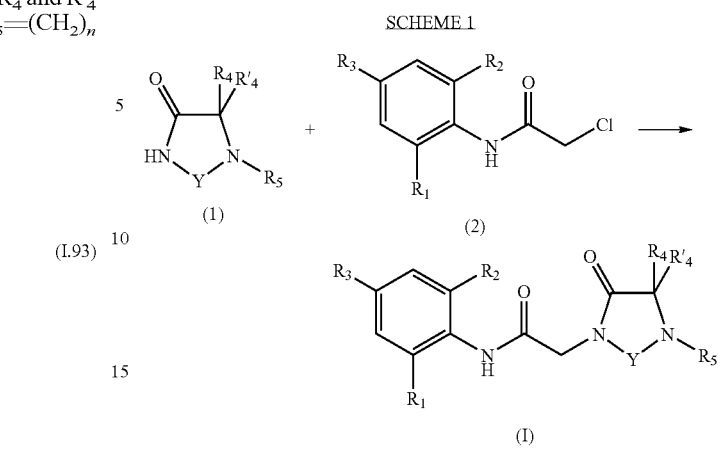

The compounds of formula (I) can be prepared by addition of the imidazolidinones or imidazolidinediones of formula (1) to the chloroacetamides of formula (2) in the presence of a base, as SCHEME 1 describes and by analogy, for example, with the reactions described in Dunbar, B. et al., *Pharmazie* 2005, 57 (7), 438, Pinza, M. et al., *J Med Chem* 1993, 36 (26), 4214, Coudert, P. et al., *Pharm Acta Helv.* 1991, 66 (5-6), 155 or Usifoh, C. O.; *Arch Pharm,* 2001, 334 (11), 366.

The imidazolidinones or imidazolidinediones of general formula 1 can be prepared according to SCHEME 2 below, in which Y, $R_4$, $R'_4$ and $R_5$ are as defined for the compounds of formula (I):

SCHEME 2

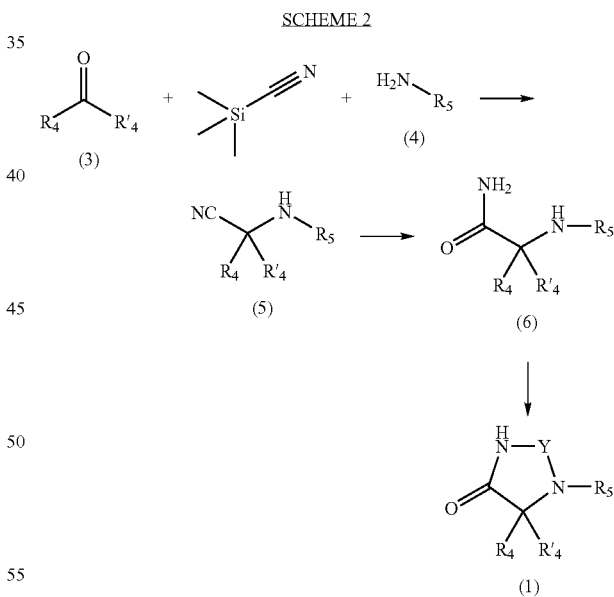

The compounds of formula (I) are obtained starting from ketones of formula (3). The latter are first reacted with the amines or anilines of formula (4) in the presence of trimethylsilyl cyanide, to give the nitrile compounds of formula (5), according, for example, to the conditions described in Matsumoto, K. et al., *Helv Chim Acta* 2005, 88 (7), 1734-1753 or Nieto, M. J. et al., *J Comb Chem* 2005, 7 (2), 258-263. The hydrolysis of the nitrile function in the presence of acid, for example, under the conditions described in Beths R. L. et al., *J. Chem. Soc.,* 1927, 1310 allows the primary amides of the formula (6) to be obtained. The cyclization, either in the presence of formaldehyde as described in Fueloep, F et al. *Pharmazie* 1992, 47 (3), 168 or Chen, F.-L.; Sung, K.; *J Heterocycl Chem* 2004, 41 (5), 697 in the case where Y=CH$_2$, either in the presence of an appropriate aryl isocyanate as described in Papadopoulos, E. P.; *J Org Chem* 1977, 42, 3925 for the case where Y=C(O) allows the imidazolidinones or the imidazolidinediones respectively of formula (I) to be obtained.

The chloroacetamides of general formula (2) can be prepared according to an amidification reaction starting from anilines of formula (7) in the presence of a base and chloroacetyl chloride, for example, as described in Davion, Y. et al., *Heterocycles* 2004, 63 (5), 1093 or Juaristy, E. et al., *J Org Chem* 1999, 64 (8), 2914, as illustrated in SCHEME 3 below in which $R_1$, $R_2$ and $R_3$ are such as defined for the compounds of formula (I):

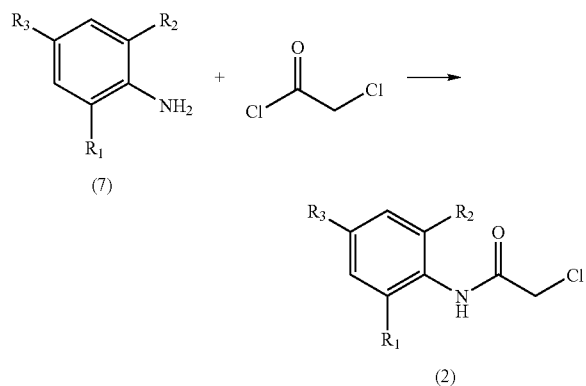

SCHEME 3

The anilines (7) are commercial compounds or are prepared according to techniques well known to one skilled in the art.

The functional groups optionally present in the reaction intermediates used in the process can be protected, either in a permanent manner or in a temporary manner, by protective groups which ensure an unequivocal synthesis of the expected compounds. The protection and deprotection reactions are carried out according to techniques well known to one skilled in the art. A temporary protective group of amines, of alcohols or of carboxylic acids means the protective groups such as those described in "Protective Groups in Organic Chemistry", ed McOmie J. W. F., Plenum Press, 1973, in "Protective Groups in Organic Synthesis" 2nd edition, Greene T. W. and Wuts P. G. M., ed John Wiley and Sons, 1991 and in "Protecting Groups", Kocienski P. J., 1994, Georg Thieme Verlag.

The compounds (I) according to the invention, as well as their pharmaceutically acceptable salts, solvates and/or hydrates, have inhibitory properties on the enzyme SOAT-1. This inhibitory activity on the enzyme SOAT-1 is measured according to a primary enzymatic test HepG2, as described in Example 64. The preferred compounds according to the present invention have a concentration allowing 50% of the response of the enzyme ($IC_{50}$) to be inhibited at less than or equal to 1000 nM, preferably at less than or equal to 300 nM, advantageously at less than or equal to 100 nM, or even at 50 nM.

The present invention also features medicaments comprising the compounds of formula (I) as described above, as well as their pharmaceutically acceptable salts, pharmaceutically acceptable solvates and/or hydrates.

The present invention also features formulating at least one compound of formula (I), and also its salts, pharmaceutically acceptable solvates and/or hydrates, into medicaments useful to prevent and/or to treat disorders of the sebaceous gland such as hyperseborrhoea, acne, seborrheic dermatitis, atopic dermatitis or rosacea, ocular pathologies such as ocular rosacea, disorders of the meibomian gland, such as blepharitis, meibomitis, chalazion, dry eye, conjunctivitis or keratoconjunctivitis, or even pathologies such as hypercholesterolaemia, arteriosclerosis or Alzheimer's disease. The compounds according to the invention are particularly suited for formulation into pharmaceutical compositions useful for the treatment of acne. The compounds according to the invention are thus suitable for use in the treatment of the pathologies listed above.

The present invention also features pharmaceutical or cosmetic compositions comprising, formulated into a physiologically acceptable carrier, at least one compound of formula (I) as defined above, or one of its salts, pharmaceutically acceptable solvates and/or hydrates. The compositions according to the invention thus comprise a physiologically acceptable carrier or at least one physiologically or pharmaceutically acceptable excipient, selected according to the cosmetic or pharmaceutical form desired and the selected mode of administration, whether regime or regimen.

Carrier or physiologically acceptable medium means a carrier compatible with the skin, the mucosa and/or the skin appendages.

The administration of the compositions according to the invention can be effected by the enteral, parenteral, rectal, topical or ocular route, whether regime or regimen. Preferably, the pharmaceutical composition is in a form suitable for application by the topical route.

By the enteral route, the composition, more particularly the pharmaceutical composition, can be in the form of tablets, of capsules, of coated tablets, of syrups, of suspensions, of powders, of granules, of emulsions, of microspheres or nanospheres or lipid or polymeric vesicles allowing controlled liberation. By the parenteral route, the composition can be in the form of solutions or suspensions for perfusion or for injection.

The compounds according to the invention contain a compound according to the invention in sufficient quantity to elicit the therapeutic, prophylactic or cosmetic effects desired. The compounds according to the invention are generally administered in a daily dose of approximately 0.001 mg/kg to 100 mg/kg of body weight, in 1 to 3 doses. The compounds are administered by the systemic route at a concentration generally ranging from 0.001 to 10% by weight, preferably from 0.01 to 2% by weight, with respect to the weight of the composition.

By the topical route, the pharmaceutical compositions according to the invention are more particularly useful for the treatment of the skin and of the mucosa and can be in the form of ointments, of creams, of milks, of pomades, of powders, of impregnated swabs, of syndets, of solutions, of gels, of sprays, of foams, of suspensions, of lotions, of sticks, of shampoos, or of washing bases. They can likewise be in the form of suspensions of microspheres or nanospheres or lipid or polymeric vesicles or polymeric patches and hydrogels allowing controlled liberation. This composition by the topical route can be present in anhydrous form, in aqueous form or in the form of an emulsion.

The compounds are administered by the topical route in a concentration generally ranging from 0.001 to 10% by weight, preferably from 0.01 to 2% by weight, with respect to the total weight of the composition.

The compounds of formula (I) according to the invention, as well as their salts, pharmaceutically acceptable solvates and/or hydrates, likewise are useful in the cosmetic field, in particular in body and hair hygiene and more particularly to combat or to prevent greasy skin or greasy hair or a greasy scalp.

The present invention thus features the cosmetic utilization of a composition comprising, in a physiologically acceptable carrier, at least one of the compounds of formula (I), optionally in the form of a salt, pharmaceutically acceptable solvate and/or hydrate, for body or hair hygiene.

The cosmetic compositions according to the invention containing, in a cosmetically acceptable carrier, at least one compound of formula (I) or one of its salts, pharmaceutically acceptable solvates and/or hydrates, can be, especially, in the form of a cream, of a milk, of a lotion, of a gel, of an ointment, of a pomade, of suspensions of microspheres or nanospheres or lipid or polymeric vesicles, of impregnated swabs, of solutions, of sprays, of foams, of sticks, of soaps, of shampoos or of washing bases.

The concentration of compound of formula (I) in the cosmetic composition ranges from 0.001 to 3% by weight, with respect to the total weight of the composition.

The pharmaceutical and cosmetic compositions as previously described can moreover contain inert, or even pharmacodynamically active, additives as far as the pharmaceutical compositions are concerned, or combinations of these additives, and especially:
 wetting agents;
 taste-improving agents;
 preservative agents such as the esters of parahydroxybenzoic acid;
 stabilizing agents;
 humidity-regulating agents;
 pH-regulating agents;
 osmotic pressure-modifying agents;
 emulsifying agents;
 UV-A and UV-B filters;
 antioxidants, such as α-tocopherol, butylhydroxyanisole or butylhydroxy-toluene, superoxide dismutase, ubiquinol or certain metal chelating agents;
 emollients;
 hydrating agents such as glycerol, PEG 400, thiamorpholinone, and its derivatives or urea;
 carotenoids and, especially, n-carotene;
 α-hydroxy acids and α-ketoacids or their derivatives, such as lactic, maleic, citric, glycolic, mandelic, tartaric, glyceric and ascorbic acids, and their salts, amides or esters or β-hydroxy acids or their derivatives, such as salicylic acid as well as its salts, amides or esters.

Of course, one skilled in the art will take care to select the possible compound(s) to add to these compositions in such a way that the properties advantageously attached intrinsically to the present invention are not, or not substantially, altered by the envisaged addition.

Furthermore, generally, the same preferences as those indicated above for the compounds of formula (I) apply mutatis mutandis to the medicaments, cosmetic and pharmaceutical compositions and utilization of the compounds of the invention.

In order to further illustrate the present invention and the advantages thereof, the following specific examples are given, including those of biological activity, it being understood that same are intended only as illustrative and in nowise limitative. In said examples to follow, all parts and percentages are given by weight, unless otherwise indicated.

The following abbreviations are used:
Ph=phenyl; Bn=benzyl; Me=methyl; Et=ethyl; Pr=propyl; iPr=isopropyl; tBu=tert-butyl; n-Pr=n-propyl; n-Bu=n-butyl; n-Pent=n-pentyl; n-Hex=n-hexyl; n-Hept=n-heptyl; n-Oct=n-octyl; n-Non=n-nonyl; m.p.=melting point
Procedures:

EXAMPLE 1

N-(2,6-Diisopropylphenyl)-2-(2,4-dioxo-1-phenyl-1,3-diazaspiro[4.4]non-3-yl)acetamide, compound (I.1) with Y=C(O); $R_1=R_2=iPr$; $R_3=H$; $R_4$ and $R'_4$ are bonded to one another to form a cyclohexyl; $R_5=Ph$

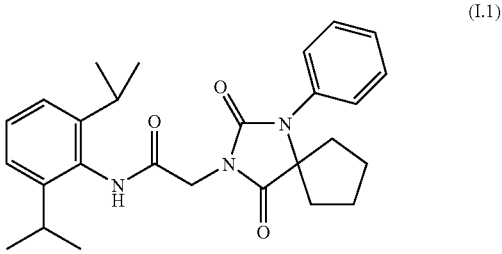

(I.1)

(a) Preparation of 2-Chloro-N-(2,6-diisopropylphenyl)acetamide 222 ml (1.59 mol) of triethylamine are added to a solution of 300 ml (1.59 mol) of 2,6-diisopropylphenylamine (starting product 1) in 1 l of dichloromethane. The reaction mixture is cooled to 0° C. and then 127 ml (1.59 mol) of chloroacetyl chloride are added, drop by drop. Once the addition is finished, the ice bath is removed and the medium is stirred for 20 min. It is then poured into water and extracted with dichloromethane. The organic phases are collected and washed with water. They are dried over sodium sulfate. The solvents are evaporated. The residue is filtered on a silica cake (eluent: dichloromethane). The filtrate is evaporated and then triturated in heptane. 345 g of 2-chloro-N-(2,6-diisopropylphenyl)acetamide are obtained in the form of a white solid. Yield=85%. M.p.=146-8° C.

(b) Preparation of 1-Phenylaminocyclopentanecarbonitrile 2.9 ml (31.8 mmol) of aniline (starting product 2) are added to a solution of 2.6 ml (29.4 mmol) of cyclopentanone (starting product 3) in 30 ml of acetic acid at 0° C. The solution is stirred for 15 minutes and 4 ml (30 mmol) of trimethylsilyl cyanide are added. The reaction medium is stirred for one night at room temperature and then gently poured into an ice-cold ammonium hydroxide solution while keeping the pH basic and extracted with dichloromethane. The organic phases are collected and washed with water. They are dried over sodium sulfate. The solvents are evaporated and then the residue is chromatographed on silica gel (heptane/ethyl acetate 90/10, v/v). 5 g of 1-phenylaminocyclopentanecarbonitrile are obtained in the form of a clear brown oil. Yield=91%.

(c) Preparation of 1-Phenylaminocyclopentanecarboxylamide 5 g (26.8 mmol) of 1-phenylaminocyclopentanecarbonitrile are dissolved in 40 ml of concentrated sulfuric acid.

The reaction medium is stirred at room temperature for 48 h and then gently poured into ice and the pH is brought to 7-8 with sodium hydroxide and the mixture is extracted with ethyl acetate. The organic phases are collected and washed with water. They are dried over sodium sulfate. The solvents are evaporated and the residue is precipitated in dichloromethane and heptane. It is then filtered and dried. 4.6 g of 1-phenylaminocyclopentanecarboxamide are obtained in the form of a white solid. Yield=84%. M.p.=159-61° C.

(d) Preparation of
1-Phenyl-1,3-diazaspiro[4.4]nonane-2,4-dione

360 µl (1.76 mmol) of 2,6-diisopropylphenyl isocyanate are added to a solution of 300 mg (1.47 mmol) of 1-phenylaminocyclopentane-carboxamide in 5 ml of toluene. The reaction medium is stirred at 200° C. for 80 min under microwave irradiation in a sealed reactor. The toluene is evaporated and the residue is purified on silica gel (heptane and then with an increasing percentage of ethyl acetate). 130 mg of 1-phenyl-1,3-diazaspiro[4.4]nonane-2,4-dione are obtained in the form of a beige solid. Yield=38%.

(e) Preparation of N-(2,6-Diisopropylphenyl)-2-(2,4-dioxo-1-phenyl-1,3-diazaspiro[4.4]non-3-yl)acetamide 80 mg (0.57 mmol) of potassium carbonate are added to a solution of 120 mg (0.52 mmol) of 1-phenyl-1,3-diazaspiro[4.4]nonane-2,4-dione and 145 mg (0.57 mmol) of 2-chloro-N-(2,6-diisopropylphenyl)acetamide in 20 ml of dimethylformamide. The reaction medium is stirred at room temperature for 24 hours. It is then poured into water and extracted with ethyl acetate. The organic phases are collected, washed with water and dried over sodium sulfate. The solvents are evaporated. The residue is chromatographed on silica gel (heptane and then heptane/ethyl acetate 80/20, v/v). 120 mg of N-(2,6-diisopropylphenyl)-2-(2,4-dioxo-1-phenyl-1,3-diazaspiro[4.4]non-3-yl)acetamide are obtained in the form of a white solid. Yield=51%, m.p.=275-7° C.

HPLC: 96.8%; Mass=447.

$^1$H NMR (CDCl$_3$; 400 Mz): 1.21 (s, 6H); 1.23 (s, 6H); 1.55 (m, 2H); 1.85 (m, 2H); 2.03-2.08 (m, 2H); 2.22-2.26 (m, 2H); 3.06-3.12 (m, 2H); 4.50 (s, 2H); 7.18-7.21 (m, 2H); 7.28-7.31 (m, 3H); 7.41-7.49 (m, 3H).

EXAMPLES 2 to 4 and 6 to 63

The synthesis of Examples 2 to 4 and 6 to 63 is described by the tables below. The compounds are synthesized following the same procedure, replacing the starting products 1, 2 and 3 of steps (a) and (b) of Example 1 by the products mentioned in the table below. The yields of these syntheses are homogeneous for the family of compounds considered.

| Ex. | IUPAC Name | Starting Product 1 | Starting Product 2 | Starting Product 3 |
|---|---|---|---|---|
| 2 | N-(2,6-Diisopropylphenyl)-2-(2,4-dioxo-1-phenyl-1,3-diazaspiro[4.5]dec-3-yl)-acetamide | 2,6-diisopropylaniline | Aniline | Cyclohexanone |
| 3 | N-Cyclohexyl-4-[2-(2,4-dioxo-1-phenyl-1,3-diazaspiro[4.5]dec-3-yl)-acetylamino]-3,5,N-trimethylbenzamide | 4-Amino-N-cyclohexyl-3,5,N-trimethylbenzamide | Aniline | Cyclohexanone |
| 4 | 4-[2-(2,4-Dioxo-1-phenyl-1,3-diazaspiro[4.5]dec-3-yl)-acetylamino]-3,5,N-trimethyl-N-phenylbenzamide | 4-Amino-N-cyclohexyl-3,5,N-trimethylbenzamide | Aniline | Cyclohexanone |
| 6 | 2-[1-(4-Chlorophenyl)-2,4-dioxo-1,3-diazaspiro[4.5]dec-3-yl]-N-(2,6-diisopropyl-phenyl)acetamide | 2,6-diisopropylaniline | 4-Chloro-phenylamine | Cyclohexanone |
| 7 | N-(2,6-Diisopropylphenyl)-2-[1-(4-fluorophenyl)-2,4-dioxo-1,3-diazaspiro[4.5]dec-3-yl]-acetamide | 2,6-diisopropylaniline | 4-Fluorophenylamine | Cyclohexanone |
| 8 | N-(2,6-Diisopropylphenyl)-2-[1-(4-methoxyphenyl)-2,4-dioxo-1,3-diazaspiro[4.5]dec-3-yl]acetamide | 2,6-diisopropylaniline | p-Anisidine | Cyclohexanone |
| 9 | N-(2,6-Diisopropylphenyl)-2-(2,4-dioxo-1-phenyl-1,3-diazaspiro[4.6]undec-3-yl)-acetamide | 2,6-diisopropylaniline | Aniline | Cycloheptanone |
| 10 | N-(2,6-Diisopropylphenyl)-2-(2,4-dioxo-1-p-tolyl-1,3-diazaspiro[4.5]dec-3-yl)-acetamide | 2,6-diisopropylaniline | p-Toluidine | Cyclohexanone |
| 11 | N-(2,6-Diisopropylphenyl)-2-[1-(3-fluorophenyl)-2,4-dioxo-1,3-diazaspiro[4.5]dec-3-yl]-acetamide | 2,6-diisopropylaniline | 3-Fluoro-phenylamine | Cyclohexanone |

| | | | | |
|---|---|---|---|---|
| 12 | 2-[1-(3-Chlorophenyl)-2,4-dioxo-1,3-diazaspiro[4.5]dec-3-yl]-N-(2,6-diisopropyl-phenyl)acetamide | 2,6-diisopropylaniline | 3-Chloro-phenylamine | Cyclohexanone |
| 13 | 2-(1-Cyclopentyl-2,4-dioxo-1,3-diazaspiro[4.5]dec-3-yl)-N-(2,6-disopropylphenyl)acetamide | 2,6-diisopropylaniline | Cyclopentylamine | Cyclohexanone |
| 14 | 2-(1-Cyclohexyl-2,4-dioxo-1,3-diazaspiro[4.5]dec-3-yl)-N-(2,6-diisopropylphenyl)-acetamide | 2,6-diisopropylaniline | Cyclohexylamine | Cyclohexanone |
| 15 | 2-(1-Cycloheptyl-2,4-dioxo-1,3-diazaspiro[4.5]dec-3-yl)-N-(2,6-diisopropylphenyl)acetamide | 2,6-diisopropylaniline | Cycloheptylamine | Cyclohexanone |
| 16 | N-(2,6-Diisopropylphenyl)-2-(2,4-dioxo-1-m-tolyl-1,3-diazaspiro[4.5]dec-3-yl)acetamide | 2,6-diisopropylamine | m-Tolylamine | Cyclohexanone |
| 17 | N-(2,6-Diisopropylphenyl)-2-[1-(4-fluorophenyl)-2,4-dioxo-1,3-diazaspiro[4.4]non-3-yl]acetamide | 2,6-diisopropylaniline | 4-Fluoroaniline | Cyclopentanone |
| 18 | N-(2,6-Diisopropylphenyl)-2-[1-(3-methoxyphenyl)-2,4-dioxo-1,3-diazaspiro[4.5]dec-3-yl]-acetamide | 2,6-diisopropylaniline | 3-Methoxy-phenylamine | Cyclohexanone |
| 19 | N-(2,6-Diisopropylphenyl)-2-[1-(2-fluorophenyl)-2,4-dioxo-1,3-diazaspiro[4.5]dec-3-yl]acetamide | 2,6-diisopropylaniline | 2-Fluoro-phenylamine | Cyclohexanone |
| 20 | 2-[1-(2-Chlorophenyl)-2,4-dioxo-1,3-diazaspiro[4.5]dec-3-yl]-N-(2,6-diisopropylphenyl)-acetamide | 2,6-diisopropylaniline | 2-Chloro-phenylamine | Cyclohexanone |
| 21 | N-(2,6-Diisopropylphenyl)-2-(2,4-dioxo-1-o-tolyl-1,3-diazaspiro[4.5]dec-3-yl)-acetamide | 2,6-diisopropylaniline | o-Tolylamine | Cyclohexanone |
| 22 | 2-(1-Benzyl-2,4-dioxo-1,3-diazaspiro[4.5]dec-3-yl)-N-(2,6-diisopropylphenyl)acetamide | 2,6-diisopropylaniline | Benzylamine | Cyclohexanone |
| 23 | N-(2,6-Diisopropylphenyl)-2-(2,4-dioxo-1-phenethyl-1,3-diazaspiro[4.5]dec-3-yl)acetamide | 2,6-diisopropylaniline | Phenethylamine | Cyclohexanone |
| 24 | 2-[1-(4-Chlorophenyl)-2,4-dioxo-1,3-diazaspiro[4.4]non-3-yl]-N-(2,6-diisopropylphenyl)-acetamide | 2,6-diisopropylaniline | 4-Chloro-phenylamine | Cyclopentanone |
| 25 | N-(2,6-Diisopropylphenyl)-2-(2,4-dioxo-1-propyl-1,3-diazaspiro[4.5]dec-3-yl)acetamide | 2,6-diisopropylaniline | Propylamine | Cyclohexanone |
| 26 | 2-(1-Butyl-2,4-dioxo-1,3-diazaspiro[4.5]dec-3-yl)-N-(2,6-diisopropylphenyl)-acetamide | 2,6-diisopropylaniline | Butylamine | Cyclohexanone |
| 27 | 2-(1-Cyclohexylmethyl-2,4-dioxo-1,3-diazaspiro[4.5]dec-3-yl)-N-(2,6-diisopropylphenyl)-acetamide acetamide | 2,6-diisopropylaniline | C-Cyclohexyl-methylamine | Cyclohexanone |
| 28 | N-(2,6-Diisopropylphenyl)-2-(1-isobutyl-2,4-dioxo-1,3-diazaspiro[4.5]dec-3-yl)acetamide | 2,6-diisopropylaniline | Isobutylamine | Cyclohexanone |
| 29 | N-(2,6-Diisopropylphenyl)-2-(2,4-dioxo-1-pentyl-1,3-diazaspiro[4.5]dec-3-yl)-acetamide | 2,6-diisopropylaniline | Pentylamine | Cyclohexanone |

-continued

| | | | | |
|---|---|---|---|---|
| 30 | N-(2,6-Diisopropylphenyl)-2-1-heptyl-2,4-dioxo-1,3-diazaspiro[4.5]dec-3-yl)acetamide | 2,6-diisopropylaniline | Heptylamine | Cyclohexanone |
| 31 | 2-(1-Cyclopropylmethyl-2,4-dioxo-1,3-diazaspiro[4.5]dec-3-yl)-N-(2,6-diisopropylphenyl)-acetamide | 2,6-diisopropylaniline | C-Cyclopropyl-methylamine | Cyclohexanone |
| 32 | N-(2,6-Diisopropylphenyl)-2-[1-(2,2-dimethylpropyl)-2,4-dioxo-1,3-diazaspiro[4,5]dec-3-yl]-acetamide | 2,6-diisopropylaniline | 2,2-Dimethyl-propylamine | Cyclohexanone |
| 33 | N-(2,6-Diisopropylphenyl)-2-[1-(2-methoxyphenyl)-2,4-dioxo-1,3-diazaspiro[4.5]dec-3-yl]-acetamide | 2,6-diisopropylaniline | 2-Methoxy-phenylamine | Cyclohexanone |
| 34 | N-(2,6-Diisopropylphenyl)-2-(2,4-dioxo-1-p-tolyl-1,3-diazaspiro[4.4]non-3-yl)acetamide | 2,6-diisopropylaniline | p-Tolylamine | Cyclopentanone |
| 35 | N-(2,6-Diisopropylphenyl)-2-(1-hexyl-2,4-dioxo-1,3-diazaspiro[4.5]dec-3-yl)acetamide | 2,6-diisopropylaniline | Hexylamine | Cyclohexanone |
| 36 | N-(2,6-Diisopropyl-phenyl)-2-[1-(4-ethylphenyl)-2,4-dioxo-1,3-diazaspiro[4.5]dec-3-yl]-acetamide | 2,6-diisopropylaniline | 4-Ethylphenylamine | Cyclohexanone |
| 37 | N-(2,6-Diisopropylphenyl)-2-[1-(4-ethylphenyl)-2,4-dioxo-1,3-diazaspiro[4.4]non-3-yl]acetamide | 2,6-diisopropylaniline | 4-Ethyl-phenylamine | Cyclopentanone |
| 38 | 2-[1-(4-Butylphenyl)-2,4-dioxo-1,3-diazaspiro[4.5]dec-3-yl]-N-(2,6-diisopropylphenyl)-acetamide | 2,6-diisopropylaniline | 4-Butyl-phenylamine | Cyclohexanone |
| 39 | 2-(4,4-Diethyl-2,5-dioxo-3-p-tolyl-imidazolidin-1-yl)-N-(2,6-diisopropylphenyl)-acetamide | 2,6-diisopropylaniline | p-Tolylamine | Pentan-3-one |
| 40 | 2-[1-(4-Butylphenyl)-2,4-dioxo-1,3-diazaspiro[4.4]non-3-yl]-N-(2,6-diisopropylphenyl)-acetamide | 2,6-diisopropylaniline | 4-Butyl-phenylamine | Cyclopentanone |
| 41 | 2-[1-(4-Benzyloxyphenyl)-2,4-dioxo-1,3-diazaspiro[4.4]non-3-yl]-N-(2,6-diisopropylphenyl)-acetamide | 2,6-diisopropylaniline | 4-Benzyloxy-phenylamine | Cyclopentanone |
| 42 | N-(2,6-Diisopropylphenyl)-2-[1-(4-hydroxymethylphenyl)-2,4-dioxo-1,3-diazaspiro[4.5]dec-3-yl]acetamide | 2,6-diisopropylaniline | (4-Amino-phenyl)-methanol | Cyclohexanone |
| 43 | N-(2,6-Diisopropylphenyl)-2-(1-nonyl-2,4-dioxo-1,3-diazaspiro[4.5]dec-3-yl)acetamide | 2,6-diisopropylaniline | Nonylamine | Cyclohexanone |
| 44 | N-(2,6-Diisopropylphenyl)-2-(1-octyl-2,4-dioxo-1,3-diazaspiro[4.5]dec-3-yl)-acetamide | 2,6-diisopropylaniline | Octylamine | Cyclohexanone |
| 45 | 2-(2,4-Dioxo-1-p-tolyl-1,3-diazaspiro[4.5]dec-3-yl)-N-(2,4,6-trimethylphenyl)-acetamide | 2,4,6-Trimethyl-phenylamine | p-Tolylamine | Cyclohexanone |
| 46 | N-(2-Chloro-6-methylphenyl)-2-(2,4-dioxo-1-p-tolyl-1,3-diazaspiro[4.5]dec-3-yl)acetamide | 2-Chloro-6-methylphenylamine | p-Tolylamine | Cyclohexanone |
| 47 | 2-(2,4-Dioxo-1-p-tolyl-1,3-diazaspiro[4.5]dec-3-yl)-N- | 2-Isopropyl-6-methylphenylamine | p-Tolylamine | Cyclohexanone |

|    |                                                                                                                                          |                                  |                         |                |
|----|------------------------------------------------------------------------------------------------------------------------------------------|----------------------------------|-------------------------|----------------|
|    | (2-isopropyl-6-methylphenyl)acetamide                                                                                                    |                                  |                         |                |
| 48 | N-(2,6-Diethylphenyl)-2-(2,4-dioxo-1-p-tolyl-1,3-diazaspiro[4.5]dec-3-yl)acetamide                                                       | 2,6-Diethyl-phenylamine          | p-Tolylamine            | Cyclohexanone  |
| 49 | N-(2,6-Diethyl-4-methylphenyl)-2-(2,4-dioxo-1-p-tolyl-1,3-diazaspiro[4.5]dec-3-yl)acetamide                                              | 2,6-Diethyl-4-methylphenylamine  | p-Tolylamine            | Cyclohexanone  |
| 50 | N-(2-Chloro-4,6-dimethylphenyl)-2-(2,4-dioxo-1-p-tolyl-1,3-diazaspiro[4.5]dec-3-yl)acetamide                                             | 2-Chloro-4,6-Dimethylphenyl-amine | p-Tolylamine            | Cyclohexanone  |
| 51 | N-(2,6-Diethylphenyl)-2-(2,4-dioxo-1-phenethyl-1,3-diazaspiro(4.5]dec-3-yl)acetamide                                                     | 2,6-Diethylphenyl-amine          | Phenethylamine          | Cyclohexanone  |
| 52 | N-(2-Bromo-4,6-dimethylphenyl)-2-(2,4-dioxo-1-p-tolyl-1,3-diazaspiro[4.5]dec-3-yl)acetamide                                              | 2-Bromo-4,6-dimethyl-phenylamine | p-Tolylamine            | Cyclohexanone  |
| 53 | N-(2-tert-Butyl-6-methylphenyl)-2-(2,4-dioxo-1-p-tolyl-1,3-diazaspiro[4.5]dec-3-yl)acetamide                                             | 2-tert-Butyl-6-methyl-phenylamine | p-Tolylamine            | Cyclohexanone  |
| 54 | N-(2,6-Diethylphenyl)-2-[1-(4-ethylphenyl)-2,4-dioxo-1,3-diazaspiro[4.5]dec-3-yl]acetamide                                               | 2,6-Diethyl-phenylamine          | 4-Ethylphenyl-amine     | Cyclohexanone  |
| 55 | N-(2,6-Diethylphenyl)-2-(2,4-dioxo-1-propyl-1,3-diazaspiro[4.5]dec-3-yl)acetamide                                                        | 2,6-Diethylphenyl-amine          | Propylamine             | Cyclohexanone  |
| 56 | 1252-[1-(4-Butylphenyl)-2,4-dioxo-1,3-diazaspiro[4.5]dec-3-yl]-N-(2,6-diethylphenyl)acetamide                                            | 2,6-Diethyl-phenylamine          | 4-Butyl-phenylamine     | Cyclohexanone  |
| 57 | N-(2,6-Diethylphenyl)-2-[1-(4-ethylphenyl)-2,4-dioxo-1,3-diazaspiro[4.4]non-3-yl]acetamide                                               | 2,6-Diethylphenyl-amine          | 4-Ethylphenyl-amine     | Cyclopentanone |
| 58 | N-(2,6-Diethylphenyl)-2-(1-heptyl-2,4-dioxo-1,3-diazaspiro[4.5]dec-3-yl)-acetamide                                                       | 2,6-Diethylphenyl-amine          | Heptylamine             | Cyclohexanone  |
| 59 | N-(2,6-Diethylphenyl)-2-(1-isobutyl-2,4-dioxo-1,3-diazaspiro[4.5]dec-3-yl)-acetamide                                                     | 2,6-Diethyl-phenylamine          | Isobutylamine           | Cyclohexanone  |
| 60 | 2-[1-(4-Benzyloxyphenyl)-2,4-dioxo-1,3-diazaspiro[4.5]dec-3-yl]-N-(2,6-diisopropylphenyl)-acetamide                                      | 2,6-diisopropylaniline           | 4-Benzyloxy-phenylamine | Cyclohexanone  |
| 61 | 2-[1-(4-Chlorophenyl)-2,4-dioxo-1,3-diazaspiro[4.4]non-3-yl]-N-(2,6-diethylphenyl)acetamide                                              | 2,6-Diethyl-phenylamine          | 4-Chloro-phenylamine    | Cyclopentanone |
| 62 | 2-[1-(4-Benzyloxyphenyl)-2,4-dioxo-1,3-diazaspiro[4.5]dec-3-yl]-N-(2,6-diethylphenyl)acetamide                                           | 2,6-Diethylphenyl-amine          | 4-Benzyloxy-phenylamine | Cyclohexanone  |
| 63 | 2-(1-Benzyl-2,4-dioxo-1,3-diazaspiro[4.5]dec-3-yl)-N-(2,6-diethylphenyl)-acetamide                                                       | 2,6-Diethyl-phenylamine          | Benzylamine             | Cyclohexanone  |

| Ex. | M.p. (° C.) | NMR |
|---|---|---|
| 2 | 245 | 1.21 (s, 6H); 1.22 (s, 6H); 1.58-1.73 (m, 6H); 1.99-2.11 (m, 4H); |

| | | |
|---|---|---|
| | | 3.06-3.11 (m, 2H); 4.47 (s. 2H); 7.18-7.33 (m, 5H); 7.39-7.48 (m, 3H) |
| 3 | 177 | — |
| 4 | 242 | 1.64 (s, 6H); 1.98-2.22 (m, 10H); 3.47 (s, 3H); 4.47 (s, 2H); 6.84 (s, 2H); 7.05-7.06 (m, 2H); 7.14-7.25 (m, 5H); 7.44-7.48 (m, 3H); 8.25 (s, 1H) |
| 6 | 237 | $CDCl_3$: 0.93-1.07 (m, 1H); 1.11 (s, 6H); 1.13 (s, 6H); 1.45-1.58 (m, 5H); 1.89-2.01 (m, 4H); 2.96-3.03 (m, 2H); 4.37 (s, 2H); 7.04-7.11 (m, 4H); 7.16-7.23 (m, 1H); 7.32-7.36 (m, 2H) |
| 7 | 258 | $CDCl_3$: 0.95-1.1 (m, 1H); 1.22 (s, 6H); 1.24 (s, 6H); 1.54-1.67 (m, 5H); 1.98-2.19 (m, 4H); 3.05-3.10 (m, 2H); 4.47 (s, 2H); 7.13-7.34 (m, 7H) |
| 8 | 193 | $CDCl_3$: 0.99-1.02 (m, 1H); 1.20 (s, 6H); 1.22 (s, 6H); 1.56-1.68 (m, 5H); 1.96-2.09 (m, 4H); 3.05-3.12 (m, 2H); 3.84 (s, 3H); 4.46 (s, 2H); 6.96-6.98 (d, 2H, J = 6.9 Hz); 7.11-7.13 (d, 2H, J = 7.1 Hz); 7.18-7.33 (m, 3H) |
| 9 | 230 | $CDCl_3$: 1.20 (s, 6H); 1.21 (s, 6H); 1.28-1.39 (m, 4H); 1.55 (m, 2H); 1.75-1.80 (m, 2H); 2.05-2.11 (m, 2H); 2.17-2.23 (m, 2H); 3.05-3.12 (m, 2H); 4.47 (s, 2H); 7.18-7.20 (d, 1H, J = 7.7 Hz); 7.27-7.31 (m, 4H); 7.33-7.46 (m, 3H) |
| 10 | 234 | $CDCl_3$: 0.99-1.02 (m, 1H); 1.20 (s, 6H); 1.22 (s, 6H); 1.60-1.72 (m, 5H); 1.96-2.10 (m, 4H); 2.41 (s, 3H); 3.05-3.10 (m, 2H); 4.47 (s, 2H); 7.07-7.09 (d, 2H, J = 7.9 Hz); 7.18-7.20 (d, 2H, J = 7.7 Hz); 7.23-7.33 (m, 3H) |
| 11 | 234 | $CDCl_3$: 1.21 (s, 6H); 1.22 (s, 6H); 1.55-1.75 (m, 4H); 2.0-2.2 (m, 6H); 3.09 (m, 2H); 4.47 (s, 2H); 6.95-7.45 (m, 7H) |
| 12 | 240 | $CDCl_3$: 1.16 (s, 6H); 1.18 (s, 6H); 1.58-1.70 (m, 4H); 2.0-2.2 (m, 6H); 3.09 (m, 2H); 4.47 (s, 2H); 7.12-7.44 (m, 7H) |
| 13 | 257 | $CDCl_3$: 1.18 (s, 6H); 1.20 (s, 6H); 1.55-1.57 (m, 2H); 1.63-1.80 (m, 10H); 1.92 (m, 2H); 2.14-2.16 (m, 4H); 3.01-3.08 (m, 2H); 3.47-3.51 (m, 1H); 4.34 (s, 2H); 7.17-7.19 (d, 2H, J = 7.7 Hz); 7.25-7.32 (m, 1H), 7.39 (s, 1H) |
| 14 | 236 | $CDCl_3$: 1.18 (s, 6H); 1.20 (s, 6H); 1.25-1.30 (m, 4H); 1.64-1.87 (m, 12H); 2.09-2.12 (m, 2H); 2.29-2.32 (m, 2H); 2.93 (m, 1H); 3.01-3.06 (m, 2H); 4.34 (s, 2H); 7.17-7.19 (d, 2H, J = 8.8 Hz); 7.25-7.32 (m, 1H); 7.43 (s, 1H) |
| 15 | 248 | $CDCl_3$: 1.18 (s, 6H); 1.20 (s, 6H); 1.39-1.50 (m, 2H); 1.59-1.80 (m, 16H); 2.08 (m, 2H); 2.34-2.38 (m, 2H); 3.01-3.09 (m, 3H); 4.34 (s, 2H); 7.17-7.18 (d, 2H, J = 7.7 Hz); 7.25-732 (m, 1H); 7.44 (s, 1H) |
| 16 | 215 | $CDCl_3$: 1.21 (s, 6H); 1.22 (s, 6H); 1.58-1.68 (m, 4H); 1.97-2.10 (m, 6H); 2.38 (s, 3H); 3.06-3.11 (m, 2H); 4.47 (s, 2H); 7.0-7.03 (m, 2H); 7.18-7.37 (m, 5H) |
| 17 | 268 | 1.15 (s, 6H); 1.17 (s, 6H); 1.46-1.50 (m, 2H); 1.79-1.81 (m, 2H); 1.95-1.98 (m, 2H); 2.15-2.20 (m, 2H); 3.00-3.05 (m, 2H); 4.43 (s, 2H); 7.08-7.15 (m, 4H); 7.19-7.28 (m, 3H) |
| 18 | 198 | $CDCl_3$: 1.12 (s, 6H); 1.14 (s, 6H); 1.53-1.60 (m, 6H); 1.89-2.02 (m, 4H); 2.97-3.02 (m, 2H); 3.74 (s, 3H); 4.38 (s, 2H); 6.64-6.73 (m, 2H); 6.85-6.95 (m, 1H); 7.09-7.30 (m, 4H) |
| 19 | 231 | $CDCl_3$: 1.20 (s, 6H); 1.22 (s, 6H); 1.55-1.68 (m, 6H); 2.04-2.09 (m, 4H); 3.05-3.12 (m, 2H); 4.49 (s, 2H); 7.18-7.33 (m, 7H) |

-continued

| | | |
|---|---|---|
| 20 | 252 | CDCl₃: 1.21 (s, 6H); 1.23 (s, 6H); 1.70-2.23 (m, 10H); 3.06-3.13 (m, 2H); 4.50 (s, 2H); 5.32 (s, 1H); 7.18-7.20 (d, 2H, J = 7.7 Hz); 7.26-7.31 (m, 2H); 7.37-7.42 (m, 2H); 7.56-7.58 (m, 1H) |
| 21 | 238 | CDCl₃: 0.88-0.92 (t, 3H); 1.21 (s, 6H); 1.23 (s, 6H); 1.28-2.30 (m, 10H); 3.07-3.14 (m, 2H); 4.48-4.49 (d, 2H); 7.13-7.39 (m, 7H) |
| 22 | 214 | CDCl₃: 1.20 (s, 6H); 1.22 (s, 6H); 1.58-1.65 (m, 5H); 1.71-1.76 (m, 3H); 2.02-2.05 (m, 2H); 3.05-3.12 (m, 2H); 4.44 (s, 2H); 4.59 (s, 2H); 7.18-7.20 (d, 2H, J = 7.7 Hz); 7.25-7.33 (m, 6H) |
| 23 | 225 | CDCl₃: 1.11 (s, 6H); 1.13 (s, 6H); 1.46-1.61 (m, 8H); 1.95-1.99 (m, 2H); 2.91-2.99 (m, 4H); 3.34-3.38 (m, 2H); 4.30 (s, 2H); 7.09-7.11 (d, 2H, J = 7.7 Hz); 7.14-7.24 (m, 6H) |
| 24 | 270 | — |
| 25 | 253 | CDCl₃: 0.93-0.97 (m, 3H); 1.19 (s, 6H); 1.20 (s, 6H); 1.65-1.73 (m, 6H); 1.78-1.81 (m, 2H); 2.08-2.12 (m, 2H); 3.01-3.08 (m, 2H); 3.19-3.23 (m, 2H); 4.37 (s, 2H); 7.17-7.18 (d, 2H, J = 7.7 Hz); 7.24-7.32 (m, 1H) |
| 26 | 241 | CDCl₃: 0.85-0.89 (t, 3H); 1.10 (s, 6H); 1.12 (s, 6H); 1.27-1.31 (m, 4H); 1.54-1.64 (m, 6H); 1.69-1.72 (m, 2H); 1.99-2.02 (m, 2H); 2.93-2.99 (m, 2H); 3.12-3.18 (m, 2H); 4.28 (s, 2H); 7.08-7.10 (d, 2H, J = 7.7 Hz); 7.15-7.23 (m, 1H) |
| 27 | 219 | CDCl₃: 0.81-0.87 (m, 2H); 1.09 (s, 6H); 1.11 (s, 6H); 1.06-1.15 (m, 4H); 1.57-1.73 (m, 13H); 1.99-2.02 (m, 2H); 2.92-3.00 (m, 4H); 4.29 (s, 2H); 7.08-7.10 (d, 2H, J = 7.7 Hz); 7.15-7.23 (m, 1H) |
| 28 | 233 | DMSO: 0.85 (s, 3H); 0.87 (s, 3H); 1.06 (s, 6H); 1.14 (s, 6H); 1.59-1.78 (m, 8H); 1.92-1.95 (m, 2H); 2.05-2.08 (m, 1H); 3.01-3.08 (m, 4H); 4.20 (s, 2H); 7.13-7.15 (d, 2H, J = 7.7 Hz); 7.23-7.27 (m, 1H); 9.50 (s, 1H) |
| 29 | 200 | DMSO: 0.80-0.84 (t, 3H); 1.05 (s, 6H); 1.08 (s, 6H); 1.15-1.30 (m, 6H); 1.48-1.70 (m, 8H); 1.84-1.96 (m, 2H); 2.98-3.08 (m, 2H); 3.15-3.24 (m, 2H); 4.65 (s, 2H); 7.10-7.12 (d, 2H); 7.20-7.24 (m, 1H); 9.44 (s, 1H) |
| 30 | 208 | CDCl₃: 0.78-0.82 (t, 3H); 1.10 (s, 6H); 1.11 (s, 6H); 1.20-1.24 (m, 10H); 1.49-1.63 (m, 6H); 1.64-1.68 (m, 2H); 1.99-2.02 (m, 2H); 2.92-2.97 (m, 2H); 3.12-3.16 (m, 2H); 4.28 (s, 2H); 7.07-7.09 (d, 1H, J = 7.7 Hz); 7.15-7.22 (m, 2H) |
| 31 | 240 | CDCl₃: 0.27-0.30 (m, 2H); 0.45-0.49 (m, 2H); 0.97-0.99 (m, 1H); 1.10 (s, 6H); 1.11 (s, 6H); 1.62-1.75 (m, 8H); 2.00-2.04 (m, 2H); 2.92-2.99 (m, 2H); 3.07-3.11 (m, 2H); 4.30 (s, 2H); 7.08-7.10 (d, 2H, J = 7.7 Hz); 7.15-7.23 (m, 1H) |
| 32 | 250 | DMSO: 0.93 (s, 9H); 1.06-1.07 (d, 6H); 1.12-1.14 (d, 6H); 1.62-1.74 (m, 8H); 1.9-2.0 (m, 2H); 3.02 (s, 2H); 3.04-3.08 (m, 2H); 4.21 (s, 2H); 7.13-7.15 (d, 2H, J = 7.7 Hz); 7.23-7.25 (m, 1H); 9.51 (s, 1H) |
| 33 | 229 | CDCl₃: 1.11 (s, 6H); 1.13 (s, 6H); 1.52-1.70 (m, 6H); 1.94-1.99 (m, 4H); 2.96-3.03 (m, 2H); 3.62 (s, 3H); 4.39 (s, 2H); 6.89-6.96 (m, 2H); 7.07-7.15 (m, 3H); 7.22-7.35 (m, 2H) |
| 34 | 278 | DMSO: 1.08-1.09 (d, 6H); 1.13-1.14 (d, 6H); 1.37-1.41 (m, 2H); 1.65-1.69 (m, 2H); 1.97-2.07 (m, 4H); 2.35 (s, 3H); 3.04-3.11 (m, 2H); 4.31 (s, 2H); |

| | | |
|---|---|---|
| | | 7.15-7.17 (d, 2H, J = 7.6 Hz); 7.23-7.30 (m, 5H); 9.55 (s, 1H) |
| 35 | 205 | DMSO: 0.85-0.88 (t, 3H); 1.06-1.08 (d, 6H); 1.12-1.14 (d, 6H); 1.27-1.29 (m, 6h); 1.5-1.67 (m, 10H); 1.85-2.0 (m, 2H); 3.04-3.07 (m, 2H); 3.16-3.18 (m, 2H); 4.19 (s, 2H); 7.13-7.15 (d, 1H, J = 7.6 Hz); 7.23-7.25 (m, 2H); 9.50 (s, 1H) |
| 36 | 221 | CDCl$_3$: 1.21 (s, 6H); 1.23 (s, 6H); 1.27-1.31 (t, 3H); 1.59-1.69 (m, 6H); 1.97-2.11 (m, 4H); 2.69-2.75 (m, 2H); 3.06-3.11 (m, 2H); 4.48 (s, 2H); 7.10-7.14 (m, 2H); 7.19-7.21 (d, 2H, J = 7.7 Hz); 7.25-7.34 (m, 3H) |
| 37 | 246 | CDCl$_3$: 1.22 (s, 6H); 1.22 (s, 6H); 1.26-1.29 (t, 3H); 1.52-1.54 (m, 2H); 1.83-1.85 (m, 2H); 2.04-2.07 (m, 2H); 2.18-2.22 (m, 2H); 2.67-2.73 (m, 2H); 3.07-3.10 (m, 2H); 4.49 (s, 2H); 7.16-7.20 (m, 4H); 7.25-7.35 (m, 3H) |
| 38 | 220 | CDCl$_3$: 0.94-0.97 (t, 3H); 1.21 (s, 6H); 1.22 (s, 6H); 1.37-1.41 (m, 2H); 1.61-1.65 (m, 8H); 1.96-2.10 (m, 4H); 2.64-2.68 (m, 2H); 3.05-3.12 (m, 2H); 4.47 (s, 2H); 7.08-7.12 (m, 2H); 7.18-7.20 (d, 1H, J = 7.7 Hz); 7.23-7.33 (m, 4H) |
| 39 | 174 | DMSO: 0.79-0.83 (t, 6H); 1.06-1.07 (d, 6H); 1.12-1.14 (d, 6H); 1.58-1.67 (m, 2H); 1.73-1.80 (m, 2H); 2.32 (s, 3H); 3.06-3.12 (m, 2H); 4.36 (s, 2H); 7.13-7.15 (d, 2H, J = 7.8 Hz); 7.18-7.28 (m, 5H); 9.62 (s, 1H) |
| 40 | 228 | DMSO: 0.88-0.91 (t, 3H); 1.08 (s, 6H); 1.11 (s, 6H); 1.28-1.38 (m, 4H); 1.55-1.66 (m, 4H); 1.96-2.03 (4H); 2.59-2.62 (m, 2H); 3.02-3.08 (m, 2H); 4.30 (s, 2H); 7.13-7.15 (d, 2H, J = 7.7 Hz); 7.18-7.30 (m, 5H); 9.53 (s, 1H) |
| 41 | 232 | DMSO: 1.10 (s, 6H); 1.13 (s, 6H); 1.35-1.45 (m, 2H); 1.65-1.75 (m, 2H); 1.95-2.10 (m, 4H); 3.05-3.15 (m, 2H); 4.31 (s, 2H); 5.14 (s, 2H); 7.10-7.12 (d, 2H, J = 9.0 Hz); 7.15-7.17 (d, 2H, J = 7.6 Hz); 7.27-7.30 (m, 3H); 7.30-7.42 (m, 3H); 7.47 (m, 2H); 9.5 (s, 1H) |
| 42 | 230 | 1.21 (s, 6H); 1.23 (s, 6H); 1.58-1.67 (m, 6H); 2.00-2.10 (m, 4H); 3.06-3.11 (m, 2H); 4.46 (s, 2H); 4.74-4.78 (t, 2H); 7.19-7.34 (m, 5H); 7.45-7.49 (m, 2H) |
| 43 | 183 | DMSO: 0.85-0.88 (t, 3H); 1.08 (s, 6H); 1.14 (s, 6H); 1.25 (m, 12H); 1.54-1.73 (m, 10H); 1.90-1.93 (m, 2H); 3.05-3.08 (m, 2H); 3.16-3.20 (m, 2H); 4.19 (s, 2H); 7.14-7.15 (d, 2H, J = 7.6 Hz); 7.23-7.27 (m, 1H); 9.49 (s, 1H) |
| 44 | 202 | DMSO: 0.85-0.88 (t, 3H); 1.08 (s, 6H); 1.14 (s, 6H); 1.27 (m, 10H); 1.54-1.76 (m, 10H); 1.90-1.93 (m, 2H); 3.03-3.10 (m, 2H); 3.16-3.20 (m, 2H); 4.19 (s, 2H); 7.14-7.15 (d, 2H, J = 7.6 Hz); 7.23-7.27 (m, 1H); 9.49 (s, 1H) |
| 45 | 266 | DMSO: 0.8-1.0 (m, 1H); 1.39-1.45 (m, 2H); 1.55 (m, 3H); 1.87-1.97 (m, 4H); 2.08 (s, 6H); 2.21 (s, 3H); 2.34 (s, 3H); 4.26 (s, 2H); 6.86 (s, 2H); 7.11-7.13 (d, 2H, J = 8.1 Hz); 7.27-7.29 (d, 2H, J = 8.03 Hz); 9.47 (s, 1H) |
| 46 | 244 | DMSO: 0.91-0.96 (m, 1H); 1.39-1.45 (m, 2H); 1.55 (m, 3H); 1.84-1.97 (m, 4H); 2.16 (s, 3H); 2.34 (s, 3H); 4.29 (s, 2H); 7.11-7.13 (d, 2H, J = 8 Hz); 7.19-7.21 (m, 2H); 7.22-7.35 (m, 3H); 9.91 (s, 1H) |
| 47 | 195 | DMSO: 0.87-0.94 (m, 1H); 1.09 (s, 3H); 1.10 (s, 3H); 1.39-1.45 (m, 2H); 1.52-1.55 (m, 3H); 1.85-1.98 (m, 4H); 2.11 (s, 3H); 2.35 (s, 3H); 3.05-3.10 (m, 1H); 4.28 (s, 2H); 7.05-7.07 (m, |

| | | |
|---|---|---|
| | | 1H); 7.11-7.19 (m, 4H); 7.27-7.29 (m, 2H); 9.54 (s, 1H) |
| 48 | 214 | DMSO: 0.85-1.0 (m, 1H); 1.08-1.12 (t, 6H); 1.41-1.47 (m, 2H); 1.54-1.57 (m, 3H); 1.90-1.99 (m, 4H); 2.36 (s, 3H); 2.47-2.53 (m, 4H); 4.29 (s, 2H); 7.09-7.22 (m, 5H); 7.29-7.31 (d, 2H, J = 8 Hz); 9.56 (s, 1H) |
| 49 | 223 | DMSO: 0.91-0.94 (m, 1H); 1.05-1.09 (t, 6H); 1.39-1.45 (m, 2H); 1.50-1.55 (3H); 1.84-1.97 (4H); 2.25 (s, 3H); 2.35 (s, 3H); 2.41-2.50 (m, 4H); 4.25 (s, 2H); 6.89 (s, 2H); 7.11-7.13 (d, 2H, J = 6.5 Hz); 7.27-7.29 (d, 2H, J = 7 Hz) |
| 50 | 248 | DMSO: 0.91-0.96 (m, 1H); 1.39-1.45 (m, 2H); 1.55 (m, 3H); 1.84-1.97 (m, 4H); 2.11 (s, 3H); 2.25 (s, 3H); 2.34 (s, 3H); 4.27 (s, 2H); 7.04 (s, 1H); 7.11-7.17 (m, 3H); 7.27-7.29 (d, 2H, J = 8 Hz); 9.80 (s, 1H) |
| 51 | 178 | DMSO: 1.08-1.11 (m, 6H); 1.17-1.24 (m, 1H); 1.53-1.68 (m, 7H); 1.85-1.88 (m, 2H); 2.47-2.52 (m, 4H); 2.85-2.89 (m, 2H); 3.33-3.42 (m, 2H); 4.21 (s, 2H); 7.08-7.09 (d, 2H, J = 7.7 Hz); 7.16-7.32 (m, 6H); 9.53 (s, 1H) |
| 52 | 245 | DMSO: 0.91-0.94 (m, 1H); 1.39-1.43 (m, 2H); 1.46-1.55 (m, 3H); 1.84-1.97 (m, 4H); 2.13 (s, 3H); 2.26 (s, 3H); 2.35 (s, 3H); 4.26 (s, 2H); 7.08 (s, 1H); 7.12-7.14 (d, 2H, J = 8.2 Hz); 7.27-7.29 (d, 2H, J = 8 Hz), 7.33 (s, 1H); 9.81 (s, 1H) |
| 53 | 120 | DMSO: 0.9-1.0 (m, 1H); 1.29 (s, 9H); 1.42-1.54 (m, 5H); 1.93 (m, 4H); 2.08 (s, 3H); 2.34 (s, 3H); 4.28 (m, 2H); 7.11-7.13 (m, 4H); 7.21-7.23 (m, 1H); 7.27-7.29 (m, 2H); 9.45 (s, 1H) |
| 54 | 188 | DMSO: 0.94 (m, 1H); 1.07-1.10 (t, 6H); 1.20-1.23 (t, 3H); 1.39-1.42 (m, 2H); 1.55 (m, 3H); 1.88-1.98 (m, 4H); 2.46-2.52 (m, 4H); 2.62-2.66 (m, 2H); 4.28 (s, 2H); 7.08-7.10 (d, 2H, J = 7.5 Hz); 7.14-7.20 (m, 3H); 7.31-7.33 (d, 2H, J = 8.05 Hz); 9.54 (s, 1H) |
| 55 | 222 | DMSO: 0.83-0.87 (t, 3H); 1.06-1.09 (t, 6H); 1.17-1.21 (m, 1H); 1.52-1.75 (m, 9H); 1.88-1.91 (m, 2H); 2.44-2.50 (m, 4H); 3.12-3.16 (m, 2H); 4.17 (s, 2H); 7.06-7.08 (d, 2H, J = 7.6 Hz); 7.15-7.18 (m, 1H); 9.50 (s, 1H) |
| 56 | 171 | DMSO: 0.89-0.93 (t, 3H); 1.07-1.11 (t, 6H); 1.31-1.59 (m, 10H); 1.88-1.97 (m, 4H); 2.46-2.52 (m, 4H); 2.60-2.64 (m, 2H); 4.28 (s, 2H); 7.08-7.22 (m, 5H); 7.29-7.31 (d, 2H, J = 8.1 Hz); 9.54 (s, 1H) |
| 57 | 191 | DMSO: 1.06-1.10 (m, 6H); 1.17-1.22 (m, 3H); 1.37-1.38 (m, 2H); 1.66-1.67 (m, 2H); 1.98-2.03 (m, 4H); 2.46-2.52 (m, 4H); 2.64-2.65 (m, 2H); 4.30 (s, 2H); 7.08-7.10 (d, 2H, J = 7.5 Hz); 7.15-7.26 (m, 3H); 7.30-7.32 (d, 2H, J = 8.2 Hz); 9.55 (s, 1H) |
| 58 | 126 | DMSO: 0.83-0.87 (t, 3H); 1.05-1.09 (t, 6H); 1.17-1.2S (m, 9H); 1.52-1.91 (m, 11H); 2.44-2.50 (m, 4H); 3.14-3.18 (m, 2H); 4.17 (s, 2H); 7.06-7.08 (d, 2H, J = 7.5 Hz); 7.14-7.18 (m, 1H); 9.50 (s, 1H) |
| 59 | 209 | DMSO: 0.84-0.86 (t, 6H); 1.05-1.09 (t, 6H); 1.17-1.21 (m, 1H); 1.58-1.76 (m, 7H); 1.87-1.92 (m, 2H); 2.04-2.05 (m, 1H); 2.44-2.50 (m, 4H); 3.00-3.02 (m, 2H); 4.18 (s, 2H); 7.06-7.08 (d, 2H, J = 7.5 Hz); 7.14-7.19 (m, 1H); 9.50 (s, 1H) |
| 60 | 118 | DMSO: 1.08 (s, 6H); 1.11 (s, 6H); 1.15-1.55 (m, 6H); 1.88-2.08 (m, 4H); 3.03-3.08 (m, 2H); 4.27 (s, 2H); 5.13 (s, 2H); 7.09-7.18 (m, 6H); |

| | | |
|---|---|---|
| | | 7.23-7.25 (m, 2H); 7.34-7.42 (m, 4H); 7.46-7.48 (d, 2H, J = 7.8 Hz); 9.52 (s, 1H) |
| 61 | 218 | DMSO: 1.06-1.10 (t, 6H); 1.41-1.43 (m, 2H); 1.66-1.68 (m, 2H); 1.94-2.09 (m, 4H); 2.45-2.51 (m, 4H); 4.30 (s, 2H); 7.07-7.09 (d, 2H, J = 7.56 Hz); 7.16-7.20 (m, 1H); 7.40-7.42 (d, 2H, J = 8.63 Hz); 7.54-7.56 (d, 2H, J = 8.61 Hz); 9.55 (s, 1H) |
| 62 | 184 | DMSO: 0.9 (m, 1H); 1.08-1.12 (t, 6H); 1.41-1.47 (m, 2H); 1.54-1.57 (m, 3H); 1.89-1.98 (m, 4H); 2.47-2.53 (m, 4H); 4.29 (s, 2H); 7.09-7.13 (m, 4H); 7.17-7.20 (m, 3H); 7.36-7.45 (m, 3H); 7.48-7.50 (m, 2H); 9.55 (s, 1H) |
| 63 | 179 | DMSO: 1.07-1.10 (t, 6H); 1.13-1.18 (m, 1H); 1.52-1.68 (m, 4H); 1.84-1.87 (m, 2H); 2.46-2.52 (m, 4H); 4.26 (s, 2H); 4.54 (s, 2H); 7.08-7.10 (d, 2H, J = 7.54 Hz); 7.16-7.24 (m, 2H); 7.27-7.31 (m, 4H); 9.56 (s, 1H) |

EXAMPLE 5

N-(2,6-Diisopropylphenyl)-2-(4-oxo-1-phenyl-1,3-diazaspiro[4.5]dec-3-yl)acetamide, compound (I.5) with $Y=CH_2$; $R_1=R_2=iPr$; $R_3=H$; $R_4$ and $R'_4$ are bonded to one another to form a cyclohexyl; $R_5=Ph$

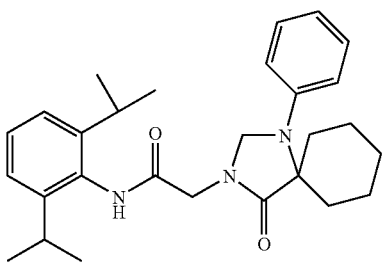

(I.5)

(a) Preparation of 1-Phenylaminocyclohexanecarbonitrile 1.4 ml (15.3 mmol) of aniline are added to a solution of 1.3 ml (12.5 mmol) of cyclohexanone in 20 ml of acetic acid at 0° C. The solution is stirred for 10 minutes and 1.9 ml (14.2 mmol) of trimethylsilyl cyanide are added. The reaction medium is stirred overnight at room temperature. It is then gently poured into a solution of ice-cold ammonium hydroxide, while keeping the pH basic, and extracted with dichloromethane. The organic phases are collected and washed with water. They are dried over sodium sulfate. The residue is precipitated in dichloromethane and heptane. The solid is filtered and dried. 2.2 g of 1-phenylaminocyclohexanecarbonitrile are obtained in the form of whitish crystals. Yield=88%, m.p.=67-9° C.

(b) Preparation of 1-Phenylaminocyclohexanecarboxylamide 5 g (25 mmol) of 1-phenylaminocyclohexanecarbonitrile are dissolved in 30 ml of concentrated sulfuric acid. The reaction medium is stirred at room temperature for 48 h. It is then gently poured into ice and the pH is brought to 7-8 with sodium hydroxide and the mixture is extracted with ethyl acetate. The organic phases are collected and washed with water. They are dried over sodium sulfate. The solvents are evaporated and the residue is precipitated in dichloromethane and heptane. It is then filtered and dried. 5.13 g of 1-phenylaminocyclohexanecarboxylamide are obtained in the form of a white solid. Yield=94%, m.p.=145-7° C.

(c) Preparation of 1-Phenyl-1,3-diazaspiro[4.5]decan-4-one 300 mg (1.37 mmol) of 1-phenylaminocyclohexanecarboxylamide are dissolved in 10 ml of methanol. 3 ml of formaldehyde and a catalytic quantity of APTS are added. The reaction medium is heated at 100° C. with microwaves for 30 min. The solvent is evaporated, and the residue is taken up with dichloromethane and washed with water. The organic phases are collected and then dried over sodium sulfate. The solvents are evaporated. The residue is chromatographed on silica gel (heptane/ethyl acetate 80/20, v/v). 50 mg of 1-phenyl-1,3-diazaspiro[4.5]decan-4-one are obtained in the form of a white solid. Yield=18%, m.p.=193-5° C.

(d) Preparation of N-(2,6-Diisopropylphenyl)-2-(4-oxo-1-phenyl-1,3-diazaspiro[4.5]dec-3-yl)acetamide 72 mg (0.52 mmol) of potassium carbonate are added to a solution of 120 mg (0.52 mmol) of 1-phenyl-1,3-diazaspiro[4.5]decan-4-one and 132 mg (0.52 mmol) of 2-chloro-N-(2,6-diisopropylphenyl)acetamide (described in Example 1 a) in 20 ml of methyl ethyl ketone. The reaction medium is stirred at room temperature for 12 hours and then for 6 h at reflux. The medium is then filtered and then the residue is chromatographed on silica gel (heptane then heptane/ethyl acetate 50/50, v/v). 135 mg of N-(2,6-diisopropylphenyl)-2-(4-oxo-1-phenyl-1,3-diazaspiro[4.5]dec-3-yl)acetamide are obtained in the form of a white solid. Yield=58%, m.p.=251-3° C.

HPLC: 98.7%; mass: 446.

$^1$H NMR (CDCl$_3$, 400 Mz): 1.20 (s, 12H); 1.36-1.37 (m, 1H); 1.71-1.74 (m, 2H); 1.81-1.84 (m, 2H); 2.09-2.14 (m, 2H); 2.25-2.28 (m, 2H); 3.03-3.05 (m, 2H); 4.26-4.27 (d, 2H); 4.90-4.91 (d, 2H); 6.97 (s, 3H); 7.19-7.20 (m, 2H); 7.33 (m, 3H); 7.84 (s, 1H).

EXAMPLE 64

Biological Tests

The compounds of formula (I) according to the invention have been subjected to a test allowing their inhibitory action with respect to the enzyme ACAT-1 to be evaluated inspired by the following publication: "Identification of ACAT1- and ACAT2-specific inhibitors using a novel, cell-based fluorescence assay: individual ACAT uniqueness", J. Lipid Res. (2004) vol. 45, pages 378-386.

The principle of this test is based on the employment of NBD-cholesterol, an analogue of cholesterol whose fluorescence depends on its environment. When this is present in a polar environment, it is weakly fluorescent although in a nonpolar environment it is strongly fluorescent. Free NBD-cholesterol locates itself in the cell membranes and is weakly fluorescent in this polar environment. When the NBD-cholesterol is esterified by ACAT, the ester of NBD-cholesterol locates itself in the nonpolar lipid droplets and is in that case strongly fluorescent.

The method below is applied: The HepG2 cells are incubated in the presence of NBD-cholesterol (1 μg/ml) and of the compound of formula (I) to be tested in black 96-well plates with a transparent base at a rate of 30 000 cells per well. After incubation for 6 h at 37° C., under 5% $CO_2$, the medium is eliminated by turning over and the cells are washed with 2 times 100 μl of PBS. After addition of 50 μl of lysis buffer ($NaPO_4$ 10 mM, Igepal 1%), the plates are stirred for 5 min and read in fluorescence (excitation 490 nm, emission 540 nm) on a FUSION apparatus (Perkin-Elmer). By way of illustration, an $IC_{50}$ of 3.2 nM is obtained for the compound (I.1), an $IC_{50}$ of 0.8 nM is obtained for the compound (I.7), an $IC_{50}$ of 0.2 nM is obtained for the compound (I.10), an $IC_{50}$ of 4.8 nM is obtained for the compound (I.14), an $IC_{50}$ of 5.6 nM is obtained for the compound (I.23), an $IC_{50}$ of 2.5 nM is obtained for the compound (I.26), an $IC_{50}$ of 0.7 nM is obtained for the compound (I.39), an $IC_{50}$ of 5.1 nM is obtained for the compound (I.46), an $IC_{50}$ of 5.3 nM is obtained for the compound (I.52) and an $IC_{50}$ of 2.7 nM is obtained for the compound (I.61).

EXAMPLE 65

Formulations

Various specific formulations based on compounds according to the invention are given below.

A-Oral Route:
(a) 0.2 g tablet:

| | |
|---|---|
| Compound (I.3) | 0.01 g |
| Starch | 0.114 g |
| Dicalcium phosphate | 0.020 g |
| Silica | 0.020 g |
| Lactose | 0.030 g |
| Talc | 0.010 g |
| Magnesium stearate | 0.005 g |

(b) Drinkable suspension in 5 ml ampoules:

| | |
|---|---|
| Compound (I.1) | 0.001 g |
| Glycerol | 0.500 g |
| 70% sorbitol | 0.500 g |
| Sodium saccharinate | 0.010 g |
| Methyl para-hydroxybenzoate | 0.040 g |
| Flavor | qs |
| Purified water | qsp 5 ml |

B-Topical Route:
(a) Ointment:

| | |
|---|---|
| Compound (I.2) | 0.300 g |
| White petroleum jelly codex | qsp 100 g |

(d) Lotion:

| | |
|---|---|
| Compound (I.4) | 0.100 g |
| Polyethylene glycol (PEG 400) | 69.900 g |
| 95% ethanol | 30.000 g |

(e) Hydrophobic ointment:

| | |
|---|---|
| Compound (I.1) | 0.300 g |
| Isopropyl myristate | 36.400 g |
| Silicone oil ("Rhodorsil 47 V 300") | 36.400 g |
| Beeswax | 13.600 g |
| Silicone oil ("Abil 300.000 cst") | qsp 100 g |

(f) Non-ionic oil-in-water cream:

| | |
|---|---|
| Compound (I.2) | 1.000 g |
| Cetyl alcohol | 4.000 g |
| Glycerol monostearate | 2.500 g |
| PEG 50 stearate | 2.500 g |
| Shea butter | 9.200 g |
| Propylene glycol | 2.000 g |
| Methyl para-hydroxybenzoate | 0.075 g |
| Propyl para-hydroxybenzoate | 0.075 g |
| Sterile demineralized water | qsp 100 g |

Each patent, patent application, publication, text and literature article/report cited or indicated herein is hereby expressly incorporated by reference in its entirety.

While the invention has been described in terms of various specific and preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. An N-phenylacetamide compound having the following general formula (I):

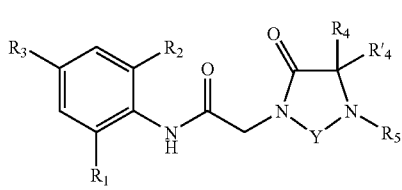

in which:
Y is C(O) or CH$_2$,
R$_1$ is a (C$_1$-C$_6$)alkyl radical,
R$_2$ is a hydrogen, chlorine, fluorine or bromine atom, or a (C$_1$-C$_6$)alkyl radical,
R$_3$ is a hydrogen atom, a (C$_1$-C$_6$)alkyl radical, or a —WNR$_6$R$_7$ radical wherein W is C(O), C(S) or CH$_2$, R$_6$ is a hydrogen atom or a (C$_1$-C$_6$)alkyl radical and R$_7$ is a hydrogen atom, a cycloalkyl radical or a phenyl radical,
R$_4$ and R'$_4$ are identical and are each a (C$_1$-C$_6$)alkyl radical or else R$_4$ and R'$_4$ are bonded to one another and together form, with the carbon atom from which they depend, a cycloalkyl group,
R$_5$ is a group selected from among:
(i) an unsubstituted phenyl radical or a phenyl radical substituted by one to three identical or different substituents selected from among the atoms fluorine, chlorine, iodine or bromine, and the radicals (C$_1$-C$_6$)alkyl, hydroxymethyl, mono-, di- or trifluoromethyl, hydroxyl, phenyl, 2-pyridyl, 3-pyridyl or 4-pyridyl, (C$_1$-C$_6$)alkoxy, phenoxy, benzyloxy, mono-, di- or trifluoromethoxy,
(ii) a (C$_1$-C$_{12}$)alkyl radical, optionally substituted by one or more hydroxyl groups, or fluorine, chlorine, iodine or bromine atoms,
(iii) a cycloalkyl radical or a -(CH$_2$)$_m$-cycloalkyl radical in which m is equal to 1, 2 or 3,
(iv) an aralkyl radical —(CH$_2$)$_n$-Ar with n equal to 1, 2 or 3 and Ar is an unsubstituted phenyl radical, unsubstituted naphthyl, or a phenyl radical substituted by one to three identical or different substituents selected from among the atoms fluorine, chlorine, iodine and bromine, and the radicals (C$_1$-C$_6$)alkyl, hydroxymethyl, mono-, di- or trifluoromethyl, hydroxyl, phenyl, 2-pyridyl, 3-pyridyl or 4-pyridyl, (C$_1$-C$_6$)alkoxy, phenoxy, benzyloxy, mono-, di- or trifluoromethoxy, and the pharmaceutically acceptable salts, conformers and rotamers thereof.

2. An N-phenylacetamide compound as defined by claim 1, wherein formula (I):
Y is C(O) or CH$_2$,
R$_1$ is a (C$_1$-C$_4$)alkyl radical,
R$_2$ is a hydrogen, fluorine, chlorine or bromine atom or a (C$_1$-C$_4$)alkyl radical,
R$_3$ is a hydrogen atom, a (C$_1$-C$_4$)alkyl radical, or a —WNR$_6$R$_7$ radical wherein W is C(O), C(S) or CH$_2$, R$_6$ is a hydrogen atom or a (C$_1$-C$_4$)alkyl radical and R$_7$ is a cycloalkyl radical having 5, 6 or 7 carbon atoms or a phenyl radical,
R$_4$ and R'$_4$ are identical and are each a (C$_1$-C$_4$)alkyl radical or else R$_4$ and R'$_4$ are bonded to one another and together form, with the carbon atom from which they depend, a cycloalkyl radical having 5, 6 or 7 carbon atoms,
R$_5$ is a group selected from among:
(i) an unsubstituted phenyl radical or phenyl substituted by one, two or three identical or different substituents selected from among the atoms fluorine, chlorine and bromine and the radicals (C$_1$-C$_4$)alkyl, trifluoromethyl, hydroxymethyl, mono-, di- and trifluoromethoxy, (C$_1$-C$_4$) alkoxy, phenoxy, benzyloxy, phenyl, 2-pyridyl, 3-pyridyl and 4-pyridyl,
(ii) a (C$_2$-C$_{12}$)alkyl radical, optionally substituted by one or more hydroxyl groups or fluorine atoms,
(iii) a cycloalkyl radical or a —CH$_2$-cycloalkyl radical,
(iv) an aralkyl radical —(CH$_2$)$_n$—Ar in which n is equal to 1, 2 or 3 and Ar is an unsubstituted phenyl radical or phenyl monosubstituted by a (C$_1$-C$_4$)alkyl, trifluoromethyl or (C$_1$-C$_4$)alkoxy radical, or a fluorine, chlorine or bromine atom.

3. An N-phenylacetamide compound as defined by claim 1, wherein formula (I), R$_1$ is a methyl, ethyl or isopropyl radical.

4. An N-phenylacetamide compound as defined by claim 1, wherein formula (I), R$_2$ is a chlorine or bromine atom or a methyl, ethyl, isopropyl or tert-butyl radical.

5. An N-phenylacetamide compound as defined by claim 1, wherein formula (I), R$_3$ is a hydrogen atom, a methyl radical or a —WNR$_6$R$_7$ radical wherein W is C(O), R$_6$ is a methyl radical and R$_7$ is a cyclohexyl radical or a phenyl radical.

6. An N-phenylacetamide compound as defined by claim 1, wherein formula (I), R$_4$ and R'$_4$ are identical and are each an ethyl or n-propyl radical, or else R$_4$ and R'$_4$ are bonded to one another and together form, with the carbon atom from which they depend, a cyclopentyl, cyclohexyl or cycloheptyl group.

7. An N-phenylacetamide compound as defined by claim 1, wherein formula (I), R$_5$ is a group selected from among:
(i) an unsubstituted phenyl radical or phenyl substituted by one, two or three identical or different substituents selected from among the chlorine or fluorine atoms, and the radicals methyl, ethyl, n-butyl, trifluoromethyl, hydroxymethyl, di- and trifluoromethoxy, methoxy, phenoxy and benzyloxy,
(ii) a sec-butyl, n-propyl, n-butyl, n-pentyl, 2,2-dimethylpropyl, n-hexyl, n-heptyl, n-octyl, n-nonyl radical, an n-butyl radical substituted in position 4 by three fluorine atoms, an n-propyl radical substituted in position 3 by three fluorine atoms, an n-butyl radical substituted in position 4 by a hydroxyl group, or an n-propyl radical substituted in position 3 by a hydroxyl group,
(iii) a —CH$_2$-cyclopropyl, —CH$_2$-cyclohexyl, cyclopentyl, cyclohexyl or cycloheptyl radical,
(iv) a radical —(CH$_2$)$_n$—Ar with n equal to 1 or 2 and Ar is an unsubstituted phenyl radical or phenyl monosubstituted, optionally in the meta or para position, by a methyl, trifluoromethyl or methoxy radical, or a fluorine atom.

8. An N-phenylacetamide compound as defined by claim 1, wherein formula (I), R$_1$ and R$_2$ are identical and are each an isopropyl radical and R$_3$ is a hydrogen atom.

9. An N-phenylacetamide compound as defined by claim 1, wherein formula (I), R$_1$ and R$_2$ are identical and are each an ethyl radical, and R$_3$ is a hydrogen atom.

10. An N-phenylacetamide compound as defined by claim 1, wherein formula (I), R$_4$ and R'$_4$ are bonded to one another and together form, with the carbon atom from which they depend, a cyclopentyl or cyclohexyl group.

11. An N-phenylacetamide compound as defined by claim 1, wherein formula (I), R$_5$ is an unsubstituted phenyl radical or phenyl substituted, in the meta or para position, by a chlorine or fluorine atom, or by a methyl or methoxy radical.

12. An N-phenylacetamide compound as defined by claim 1, wherein formula (I), Y is C(O).

13. An N-phenylacetamide compound as defined by claim 1, selected from among the following compounds, pharmaceutically acceptable salts, conformers and rotamers thereof:

N-(2,6-Diisopropylphenyl)-2-(2,4-dioxo-1-phenyl-1,3-diazaspiro[4.4]non-3-yl)acetamide, N-(2,6-Diisopropylphenyl)-2-(2,4-dioxo-1-phenyl-1,3-diazaspiro[4.5]dec-3-yl)acetamide, N-Cyclohexyl-4-[2-(2,4-dioxo-1-phenyl-1,3-diazaspiro[4.5]dec-3-yl)acetylamino]-3,5,N-trimethylbenzamide, 4-[2-(2,4-Dioxo-1-phenyl-1,3-diazaspiro[4.5]dec-3-yl)acetylamino]-3,5,N-trimethyl-N-phenylbenzamide, N-(2,6-Diisopropylphenyl)-2-(4-oxo-1-phenyl-1,3-diazaspiro[4.5]dec-3-yl)acetamide, 2-[1-(4-Chlorophenyl)-2,4-dioxo-1,3-diazaspiro[4.5]dec-3-yl]-N-(2,6-di-isopropylphenyl)acetamide, N-(2,6-Diisopropylphenyl)-2-[1-(4-fluorophenyl)-2,4-dioxo-1,3-diazaspiro[4.5]dec-3-yl]acetamide, N-(2,6-Diisopropylphenyl)-2-[1-(4-methoxyphenyl)-2,4-dioxo-1,3-diazaspiro[4.5]dec-3-yl]acetamide, N-(2,6-Diisopropylphenyl)-2-(2,4-dioxo-1-phenyl-1,3-diazaspiro[4.6]undec-3-yl)acetamide, N-(2,6-Diisopropylphenyl)-2-(2,4-dioxo-1-p-tolyl-1,3-diazaspiro[4.5]dec-3-yl)acetamide, N-(2,6-Diisopropylphenyl)-2-[1-(3-fluorophenyl)-2,4-dioxo-1,3-diazaspiro[4.5]dec-3-yl]acetamide, 2-[1-(3-Chlorophenyl)-2,4-dioxo-1,3-diazaspiro[4.5]dec-3-yl]-N-(2,6-diisopropylphenyl)acetamide, 2-(1-Cyclopentyl-2,4-dioxo-1,3-diazaspiro[4.5]dec-3-yl)-N-(2,6-diisopropylphenyl)acetamide, 2-(1-Cyclohexyl-2,4-dioxo-1,3-diazaspiro[4.5]dec-3-yl)-N-(2,6-diisopropylphenyl)acetamide, 2-(1-Cycloheptyl-2,4-dioxo-1,3-diazaspiro[4.5]dec-3-yl)-N-(2,6-diisopropylphenyl)acetamide, N-(2,6-Diisopropylphenyl)-2-(2,4-dioxo-1-m-tolyl-1,3-diazaspiro[4.5]dec-3-yl)acetamide, N-(2,6-Diisopropylphenyl)-2-[1-(4-fluorophenyl)-2,4-dioxo-1,3-diazaspiro[4.4]non-3-yl]acetamide, N-(2,6-Diisopropylphenyl)-2-[1-(3-methoxyphenyl)-2,4-dioxo-1,3-diazaspiro[4.5]dec-3-yl]acetamide, N-(2,6-Diisopropylphenyl)-2-[1-(2-fluorophenyl)-2,4-dioxo-1,3-diazaspiro[4.5]dec-3-yl]acetamide, 2-[1-(2-Chlorophenyl)-2,4-dioxo-1,3-diazaspiro[4.5]dec-3-yl]-N-(2,6-di-isopropylphenyl)acetamide, N-(2,6-Diisopropylphenyl)-2-(2,4-dioxo-1-o-tolyl-1,3-diazaspiro[4.5]dec-3-yl)acetamide, 2-(1-Benzyl-2,4-dioxo-1,3-diazaspiro[4.5]dec-3-yl)-N-(2,6-diisopropylphenyl)acetamide, N-(2,6-Diisopropylphenyl)-2-(2,4-dioxo-1-phenethyl-1,3-diazaspiro[4.5]dec-3-yl)acetamide, 2-[1-(4-Chlorophenyl)-2,4-dioxo-1,3-diazaspiro[4.4]non-3-yl]-N-(2,6-diisopropylphenyl)acetamide, N-(2,6-Diisopropylphenyl)-2-(2,4-dioxo-1-propyl-1,3-diazaspiro[4.5]dec-3-yl)acetamide, 2-(1-Butyl-2,4-dioxo-1,3-diazaspiro[4.5]dec-3-yl)-N-(2,6-diisopropylphenyl)acetamide, 2-(1-Cyclohexylmethyl-2,4-dioxo-1,3-diazaspiro[4.5]dec-3-yl)-N-(2,6-diisopropylphenyl)-acetamide, N-(2,6-Diisopropylphenyl)-2-(1-isobutyl-2,4-dioxo-1,3-diazaspiro[4.5]dec-3-yl)acetamide, N-(2,6-Diisopropylphenyl)-2-(2,4-dioxo-1-pentyl-1,3-diazaspiro[4.5]dec-3-yl)acetamide, N-(2,6-Diisopropylphenyl)-2-(1-heptyl-2,4-dioxo-1,3-diazaspiro[4.5]dec-3-yl)acetamide, 2-(1-Cyclopropyl methyl-2,4-dioxo-1,3-diazaspiro[4.5]dec-3-yl)-N-(2,6-di-isopropylphenyl)acetamide, N-(2,6-Diisopropylphenyl)-2-[1-(2,2-dimethylpropyl)-2,4-dioxo-1,3-diazaspiro[4.5]dec-3-yl]acetamide, N-(2,6-Diisopropylphenyl)-2-[1-(2-methoxyphenyl)-2,4-dioxo-1,3-diazaspiro[4.5]dec-3-yl]acetamide, N-(2,6-Diisopropylphenyl)-2-(2,4-dioxo-1-p-tolyl-1,3-diazaspiro[4.4]non-3-yl)acetamide, N-(2,6-Diisopropylphenyl)-2-(1-hexyl-2,4-dioxo-1,3-diazaspiro[4.5]dec-3-yl)acetamide, N-(2,6-Diisopropylphenyl)-2-[1-(4-ethylphenyl)-2,4-dioxo-1,3-diazaspiro[4.5]dec-3-yl]acetamide, N-(2,6-Diisopropylphenyl)-2-[1-(4-ethylphenyl)-2,4-dioxo-1,3-diazaspiro[4.4]non-3-yl]acetamide, 2-[1-(4-Butylphenyl)-2,4-dioxo-1,3-diazaspiro[4.5]dec-3-yl]-N-(2,6-diisopropylphenyl)acetamide, 2-(4,4-Diethyl-2,5-dioxo-3-p-tolylimidazolidin-1-yl)-N-(2,6-diisopropylphenyl)acetamide, 2-[1-(4-Butylphenyl)-2,4-dioxo-1,3-diazaspiro[4.4]non-3-yl]-N-(2,6-diisopropylphenyl)acetamide, 2-[1-(4-Benzyloxyphenyl)-2,4-dioxo-1,3-diazaspiro[4.4]non-3-yl]-N-(2,6-di-isopropylphenyl)acetamide, N-(2,6-Diisopropylphenyl)-2-[1-(4-hydroxymethylphenyl)-2,4-dioxo-1,3-diazaspiro[4.5]dec-3-yl]acetamide, N-(2,6-Diisopropylphenyl)-2-(1-nonyl-2,4-dioxo-1,3-diazaspiro[4.5]dec-3-yl)acetamide, N-(2,6-Diisopropylphenyl)-2-(1-octyl-2,4-dioxo-1,3-diazaspiro[4.5]dec-3-yl)acetamide, 2-(2,4-Dioxo-1-p-tolyl-1,3-diazaspiro[4.5]dec-3-yl)-N-(2,4,6-trimethylphenyl)acetamide, N-(2-Chloro-6-methylphenyl)-2-(2,4-dioxo-1-p-tolyl-1,3-diazaspiro[4.5]dec-3-yl)acetamide, 2-(2,4-Dioxo-1-p-tolyl-1,3-diazaspiro[4.5]dec-3-yl)-N-(2-isopropyl-6-methylphenyl)acetamide, N-(2,6-Diethylphenyl)-2-(2,4-dioxo-1-p-tolyl-1,3-diazaspiro[4.5]dec-3-yl)-acetamide, N-(2,6-Diethyl-4-methylphenyl)-2-(2,4-dioxo-1-p-tolyl-1,3-diazaspiro[4.5]dec-3-yl)acetamide, N-(2-Chloro-4,6-dimethylphenyl)-2-(2,4-dioxo-1-p-tolyl-1,3-diazaspiro[4.5]dec-3-yl)acetamide, N-(2,6-Diethylphenyl)-2-(2,4-dioxo-1-phenethyl-1,3-diazaspiro[4.5]dec-3-yl)acetamide, N-(2-Bromo-4,6-dimethylphenyl)-2-(2,4-dioxo-1-p-tolyl-1,3-diazaspiro[4.5]dec-3-yl)acetamide, N-(2-tert-Butyl-6-methylphenyl)-2-(2,4-dioxo-1-p-tolyl-1,3-diazaspiro[4.5]dec-3-yl)acetamide, N-(2,6-Diethylphenyl)-2-[1-(4-ethylphenyl)-2,4-dioxo-1,3-diazaspiro[4.5]dec-3-yl]acetamide, N-(2,6-Diethylphenyl)-2-(2,4-dioxo-1-propyl-1,3-diazaspiro[4.5]dec-3-yl)acetamide, 2-[1-(4-Butylphenyl)-2,4-dioxo-1,3-diazaspiro[4.5]dec-3-yl]-N-(2,6-diethylphenyl)acetamide, N-(2,6-Diethylphenyl)-2-[1-(4-ethylphenyl)-2,4-dioxo-1,3-diazaspiro[4.4]non-3-yl]acetamide, N-(2,6-Diethylphenyl)-2-(1-heptyl-2,4-dioxo-1,3-diazaspiro[4.5]dec-3-yl)-acetamide, N-(2,6-Diethylphenyl)-2-(1-isobutyl-2,4-dioxo-1,3-diazaspiro[4.5]dec-3-yl)-acetamide, 2-[1-(4-Benzyloxyphenyl)-2,4-dioxo-1,3-diazaspiro[4.5]dec-3-yl]-N-(2,6-di-isopropylphenyl)acetamide, 2-[1-(4-Chlorophenyl)-2,4-dioxo-1,3-diazaspiro[4.4]non-3-yl]-N-(2,6-di-ethylphenyl)acetamide, 2-[1-(4-Benzyloxyphenyl)-2,4-dioxo-1,3-diazaspiro[4.5]dec-3-yl]-N-(2,6-di-ethylphenyl)acetamide, 2-(1-Benzyl-2,4-dioxo-1,3-diazaspiro[4.5]dec-3-yl)-N-(2,6-diethylphenyl)acetamide, N-(2,6-Diisopropylphenyl)-2-[2,4-dioxo-1-(4-trifluoromethylphenyl)-1,3-diazaspiro[4.5]dec-3-yl]acetamide, N-(2,6-Diisopropylphenyl)-2-[2,4-dioxo-1-(3-trifluorom-
ethylphenyl)-1,3-diazaspiro[4.5]dec-3-yl]acetamide,
N-(2,6-Diisopropylphenyl)-2-[2,4-dioxo-1-(2-trifluorom-
ethylphenyl)-1,3-diazaspiro[4.5]dec-3-yl]acetamide,
2-[1-(4-Difluoromethoxyphenyl)-2,4-dioxo-1,3-diaza-
spiro[4.5]dec-3-yl]-N-(2,6-diisopropylphenyl)aceta-
mide,
2-[1-(4-Trifluoromethoxyphenyl)-2,4-dioxo-1,3-diaza-
spiro[4.5]dec-3-yl]-N-(2,6-diisopropylphenyl)aceta-
mide,
N-(2,6-Diisopropylphenyl)-2-[1-(3,4-dimethylphenyl)-2,
4-dioxo-1,3-diazaspiro[4.5]dec-3-yl]acetamide,
N-(2,6-Diisopropylphenyl)-2-[1-(2,4-dimethylphenyl)-2,
4-dioxo-1,3-diazaspiro[4.5]dec-3-yl]acetamide,
N-(2,6-Diisopropylphenyl)-2-[1-(3-fluoro-4-methylphe-
nyl)-2,4-dioxo-1,3-diazaspiro[4.5]dec-3-yl]acetamide,
N-(2,6-Diisopropylphenyl)-2-[1-(4-methyl-3-trifluorom-
ethylphenyl)-2,4-dioxo-1,3-diazaspiro[4.5]dec-3-yl]
acetamide,
N-(2,6-Diisopropylphenyl)-2-[1-(3,5-difluoro-4-meth-
ylphenyl)-2,4-dioxo-1,3-diazaspiro[4.5]dec-3-yl]aceta-
mide,
N-(2,6-Diisopropylphenyl)-2-[1-(2-fluoro-4-methylphe-
nyl)-2,4-dioxo-1,3-diazaspiro[4.5]dec-3-yl]acetamide,
N-(2,6-Diisopropylphenyl)-2-[1-(4-fluoro-3-methylphe-
nyl)-2,4-dioxo-1,3-diazaspiro[4.5]dec-3-yl]acetamide,
N-(2,6-Diisopropylphenyl)-2-[1-(4-chloro-3-methylphe-
nyl)-2,4-dioxo-1,3-diazaspiro[4.5]dec-3-yl]acetamide,
N-(2,6-Diisopropylphenyl)-2-[2,4-dioxo-1-(3-phenox-
yphenyl)-1,3-diazaspiro[4.5]dec-3-yl]acetamide,
N-(2,6-Diisopropylphenyl)-2-(2,5-dioxo-4,4-dipropyl-3-
p-tolylimidazolidin-1-yl)acetamide,
2-(4,4-Dibutyl-2,5-dioxo-3-p-tolylimidazolidin-1-yl)-N-
(2,6-diisopropylphenyl)acetamide,
N-(2,6-Diisopropylphenyl)-2-[2,4-dioxo-1-(4,4,4-trifluo-
robutyl)-1,3-diazaspiro[4.5]dec-3-yl]acetamide,
N-(2,6-Diisopropylphenyl)-2-[2,4-dioxo-1-(4,4,4-trifluo-
ropropyl)-1,3-diazaspiro[4.5]dec-3-yl]acetamide,
N-(2,6-Diisopropylphenyl)-2-[1-(3-hydroxypropyl)-2,4-
dioxo-1,3-diazaspiro[4.5]dec-3-yl]acetamide,
N-(2,6-Diisopropylphenyl)-2-[1-(3-hydroxybutyl)-2,4-di-
oxo-1,3-diazaspiro[4.5]dec-3-yl]acetamide,
N-(2,6-Diisopropylphenyl)-2-[1-(4-fluorobenzyl)-2,4-di-
oxo-1,3-diazaspiro[4.5]dec-3-yl]acetamide,
N-(2,6-Diisopropylphenyl)-2-[1-(4-methylbenzyl)-2,4-
dioxo-1,3-diazaspiro[4.5]dec-3-yl]acetamide,
N-(2,6-Diisopropylphenyl)-2-[2,4-dioxo-1-(4-trifluorom-
ethylbenzyl)-1,3-diazaspiro[4.5]dec-3-yl]acetamide,
N-(2,6-Diisopropylphenyl)-2-[1-(3-methylbenzyl)-2,4-
dioxo-1,3-diazaspiro[4.5]dec-3-yl]acetamide,
N-(2,6-Diisopropylphenyl)-2-[1-(3-fluorobenzyl)-2,4-di-
oxo-1,3-diazaspiro[4.5]dec-3-yl]acetamide,
N-(2,6-Diisopropylphenyl)-2-[1-(3-methoxybenzyl)-2,4-
dioxo-1,3-diazaspiro[4.5]dec-3-yl]acetamide,
N-(2,6-Diisopropylphenyl)-2-[2,4-dioxo-1-(3-trifluorom-
ethylbenzyl)-1,3-diazaspiro[4.5]dec-3-yl]acetamide,
N-(2,6-Diisopropylphenyl)-2-[1-(2-methylbenzyl)-2,4-
dioxo-1,3-diazaspiro[4.5]dec-3-yl]acetamide,
N-(2,6-Diisopropylphenyl)-2-[1-(2-fluorobenzyl)-2,4-di-
oxo-1,3-diazaspiro[4.5]dec-3-yl]acetamide, and
N-(2,6-Diisopropylphenyl)-2-[2,4-dioxo-1-(2-trifluorom-
ethylbenzyl)-1,3-diazaspiro[4.5]dec-3-yl]acetamide.

14. A medicament comprising at least one N-phenylaceta-
mide compound as defined by claim 1, or salt, conformer or
rotamer thereof.

15. A pharmaceutical composition comprising, formulated
into a physiologically acceptable carrier, at least one N-phe-
nylacetamide compound as defined by claim 1, or salt, con-
former or rotamer thereof.

16. A pharmaceutical composition as defined by claim 15,
comprising a concentration of compound(s) of formula (I)
ranging from 0.001 to 10% by weight relative to the total
weight thereof.

17. A pharmaceutical composition as defined by claim 16,
comprising a concentration of compound(s) of formula (I)
ranging from 0.01 to 2% by weight relative to the total weight
thereof.

18. A cosmetic composition comprising, formulated into a
physiologically acceptable carrier, at least one N-phenylac-
etamide compound as defined by claim 1, or salt, conformer
or rotamer thereof.

19. A cosmetic composition as defined by claim 18, com-
prising a concentration of compound(s) of formula (I) rang-
ing from 0.001 to 3% by weight relative to the total weight
thereof.

20. A pharmaceutical composition as defined by claim 15,
formulated for topical application.

21. A pharmaceutical composition as defined by claim 20,
comprising a cream, a milk, a lotion, a gel, an ointment, a
pomade, suspensions of microspheres or nanospheres or lipid
or polymeric vesicles, impregnated swabs, solutions, sprays,
foams, sticks, soaps, shampoos or washing bases.

22. A cosmetic composition as defined by claim 18, for-
mulated for body or hair hygiene.

23. A regime or regimen for preventing or treating disor-
ders of the sebaceous gland, hyperseborrhoea, acne, sebor-
rhoeic dermatitis, atopic dermatitis, rosacea, ocular rosacea,
blepharitis, meibomitis, chalazion, dry eye, conjunctivitis,
keratoconjunctivitis, hypercholesterolaemia, arteriosclerosis
or Alzheimer's disease, comprising administering to an indi-
vidual in need of such treatment, for such period of time as
required to elicit the desired result, a thus effective amount of
at least one N-phenylacetamide compound as defined by
claim 1, or salt, conformer or rotamer thereof.

24. The regime or regimen as defined by claim 23, com-
prising the treatment of acne.

* * * * *